(12) United States Patent
Joseph et al.

(10) Patent No.: US 11,364,346 B2
(45) Date of Patent: Jun. 21, 2022

(54) PRECISION LOW-DOSE, LOW-WASTE SYRINGES AND ERGONOMIC ATTACHMENTS THEREFOR

(71) Applicant: Innomed Technologies, Inc., Encino, CA (US)

(72) Inventors: John H. Joseph, Westlake Village, CA (US); Minh Bui, Stanton, CA (US); Rod Peterson, Ladera Ranch, CA (US)

(73) Assignee: Innomed Technologies, Inc., Encino, CA (US)

( * ) Notice: Subject to any disclaimer, the term of this patent is extended or adjusted under 35 U.S.C. 154(b) by 430 days.

(21) Appl. No.: 16/268,472

(22) Filed: Feb. 5, 2019

(65) Prior Publication Data

US 2019/0381252 A1 Dec. 19, 2019

Related U.S. Application Data

(63) Continuation-in-part of application No. 16/120,122, filed on Aug. 31, 2018, now Pat. No. 10,391,253.
(Continued)

(51) Int. Cl.
*A61M 5/315* (2006.01)
*A61M 5/31* (2006.01)

(52) U.S. Cl.
CPC ...... *A61M 5/3137* (2013.01); *A61M 5/31573* (2013.01); *A61M 5/31586* (2013.01); *A61M 2005/3139* (2013.01)

(58) Field of Classification Search
CPC ............ A61M 5/31526; A61M 5/3137; A61M 5/31528; A61M 5/31531; A61M 5/31575;
(Continued)

(56) References Cited

U.S. PATENT DOCUMENTS 1,564,048 A 12/1925 Cook
3,325,061 A 6/1967 Ellsworth
(Continued)

FOREIGN PATENT DOCUMENTS

DE 19732909 A1 2/1999
JP 0880350 A 3/1996

OTHER PUBLICATIONS

Earp, Ana Paula De Sa, and Ellen S. Marmur. "The Five D's of Botulinum Toxin: Doses, Dilution, Diffusion, Duration and Dogma." Journal of Cosmetic and Laser Therapy, vol. 10, No. 2, 2008, pp. 93-102., doi:10.1080/14764170701883660. (Year: 2008).
(Continued)

*Primary Examiner* — James D Ponton
(74) *Attorney, Agent, or Firm* — Rollins IP; John F. Rollins

(57) ABSTRACT

Syringe attachments and syringes have particular suitability to the precision dispensing of small amounts of high viscosity materials, such as dermal fillers. Syringes and attachments may include precision position indicators viewed from multiple positions to enable a user to determine plunger position and the amount of dispensed contents with precision. A configuration of the attachment may be slidably secured to a syringe to permit a user to operate the syringe from a lateral position using sliding movement of the thumb and fingers of one hand, for example. This configuration may be particularly suitable for self-administered insulin injections.

19 Claims, 25 Drawing Sheets

Related U.S. Application Data

(60) Provisional application No. 62/686,915, filed on Jun. 19, 2018.

(58) Field of Classification Search
CPC ...... A61M 5/31581; A61M 2005/3139; A61M 2005/3152
See application file for complete search history.

(56) References Cited

U.S. PATENT DOCUMENTS

| | | | |
|---|---|---|---|
| 4,178,071 A | 12/1979 | Asbell | |
| 5,830,152 A * | 11/1998 | Tao | A61B 10/0233 600/562 |
| 6,004,297 A | 12/1999 | Steenfeldt-Jensen et al. | |
| 6,074,372 A | 6/2000 | Hansen | |
| 7,611,495 B1 | 11/2009 | Gianturco | |
| 2006/0217670 A1 | 9/2006 | Cecchi et al. | |
| 2008/0262435 A1 * | 10/2008 | Erickson | A61M 5/31531 604/192 |
| 2009/0043255 A1 | 2/2009 | Taufig | |
| 2010/0305501 A1 | 12/2010 | Ratjen | |
| 2013/0090603 A1 | 4/2013 | Hoyle, Jr. | |
| 2013/0197449 A1 | 8/2013 | Franklin | |
| 2013/0218293 A1 | 8/2013 | Mita et al. | |
| 2015/0196714 A1 * | 7/2015 | Creaturo | A61M 5/3243 604/198 |
| 2016/0243313 A1 * | 8/2016 | Tran | A61B 17/00491 |
| 2018/0146985 A1 | 5/2018 | Field | |
| 2019/0111211 A1 | 4/2019 | Verhoeven et al. | |

OTHER PUBLICATIONS

International Search Report and Written Opinion of the International Search Authority in PCT/US2019/038041 dated Nov. 13, 2019.

EP Application 19822440.4, Extended European Search Report dated Feb. 15, 2022.

European Application No. 19822440.4, Extended European Search Report dated Feb. 15, 2022.

* cited by examiner

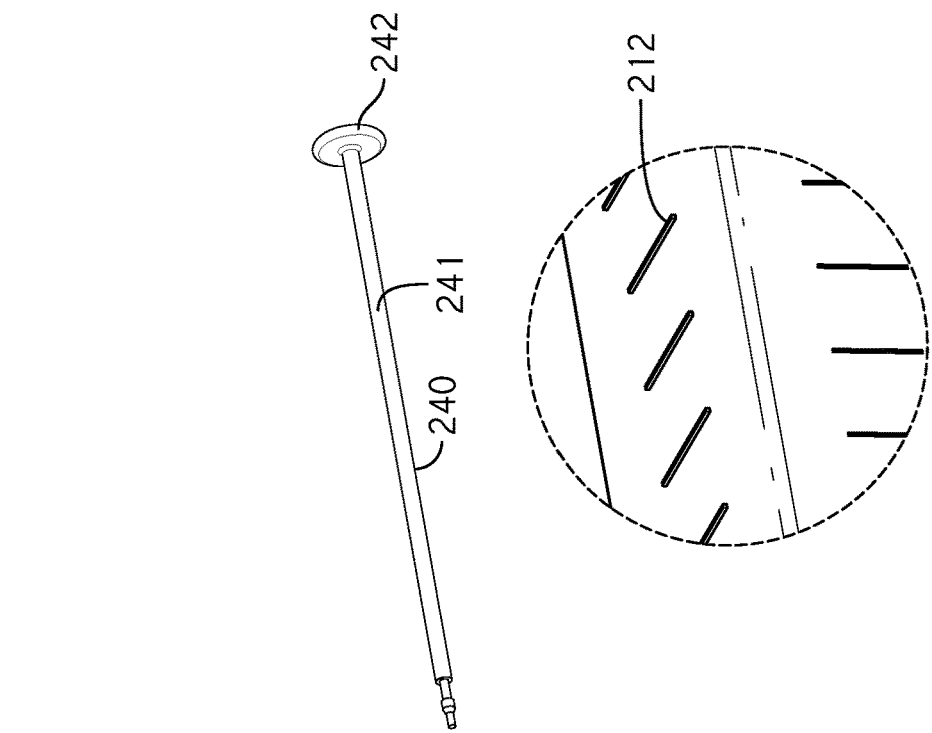
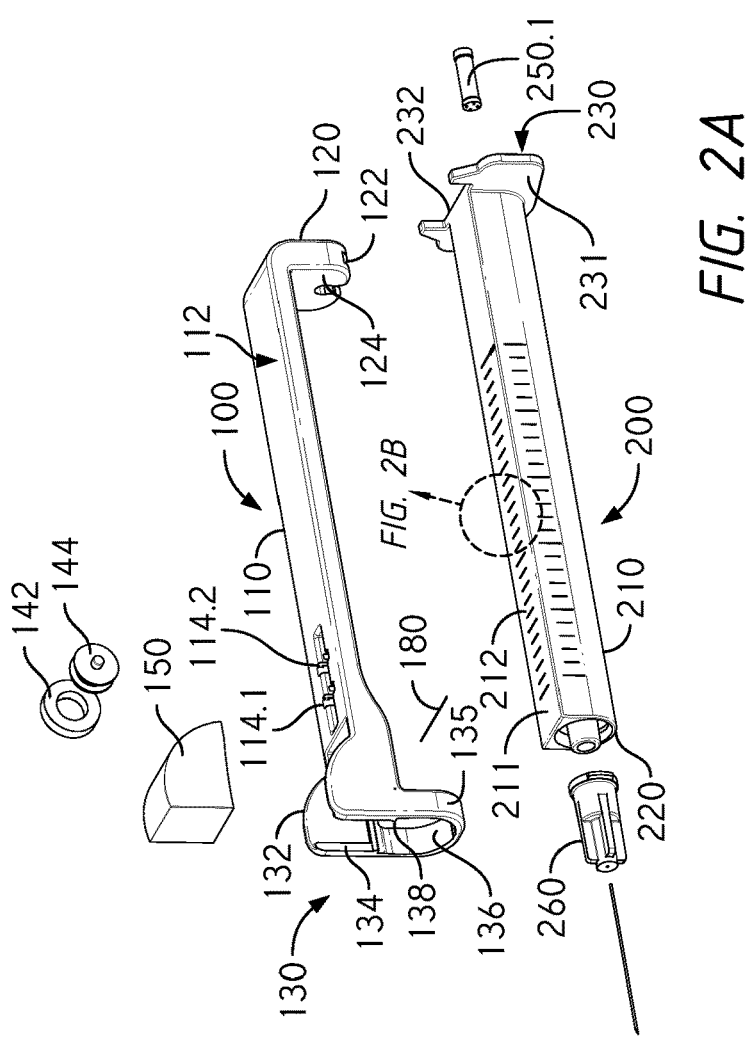
FIG. 2B
FIG. 2A

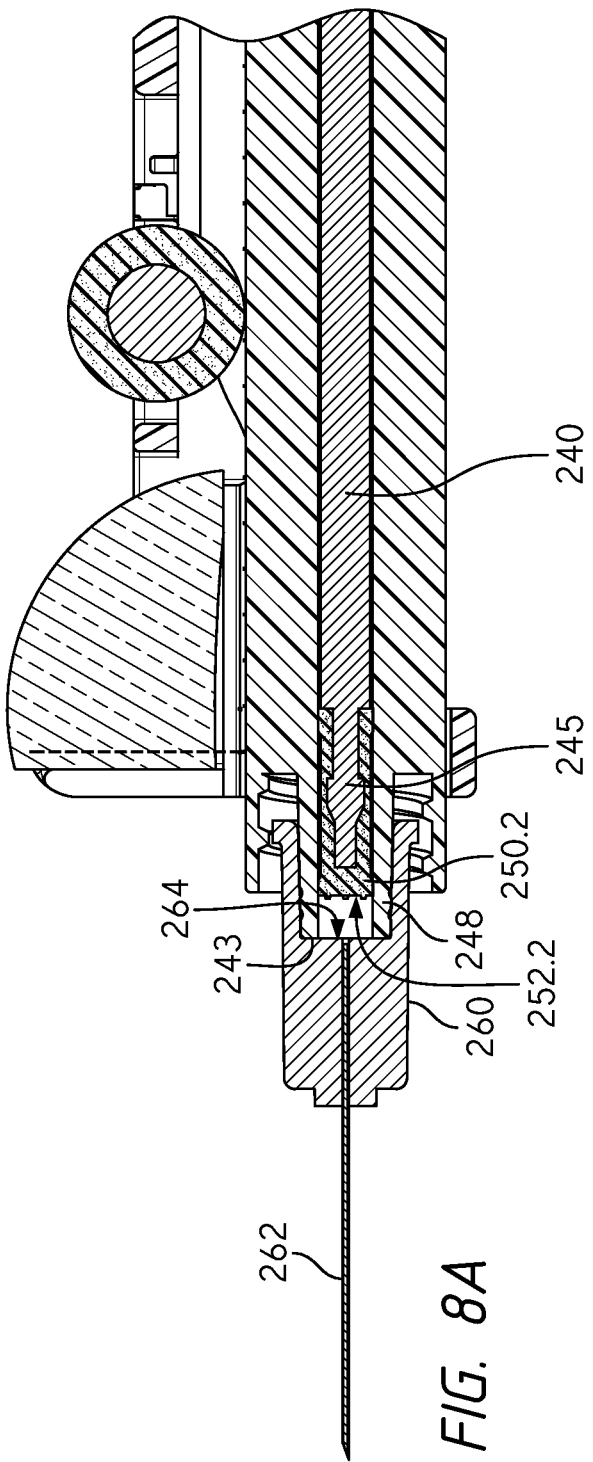
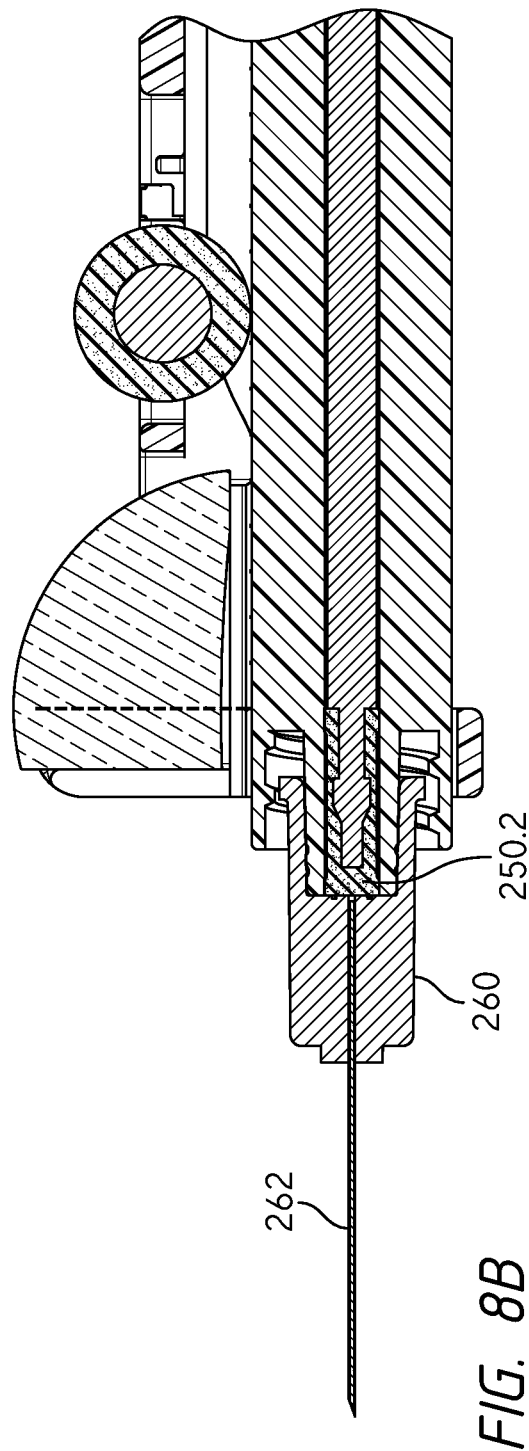
FIG. 8A
FIG. 8B

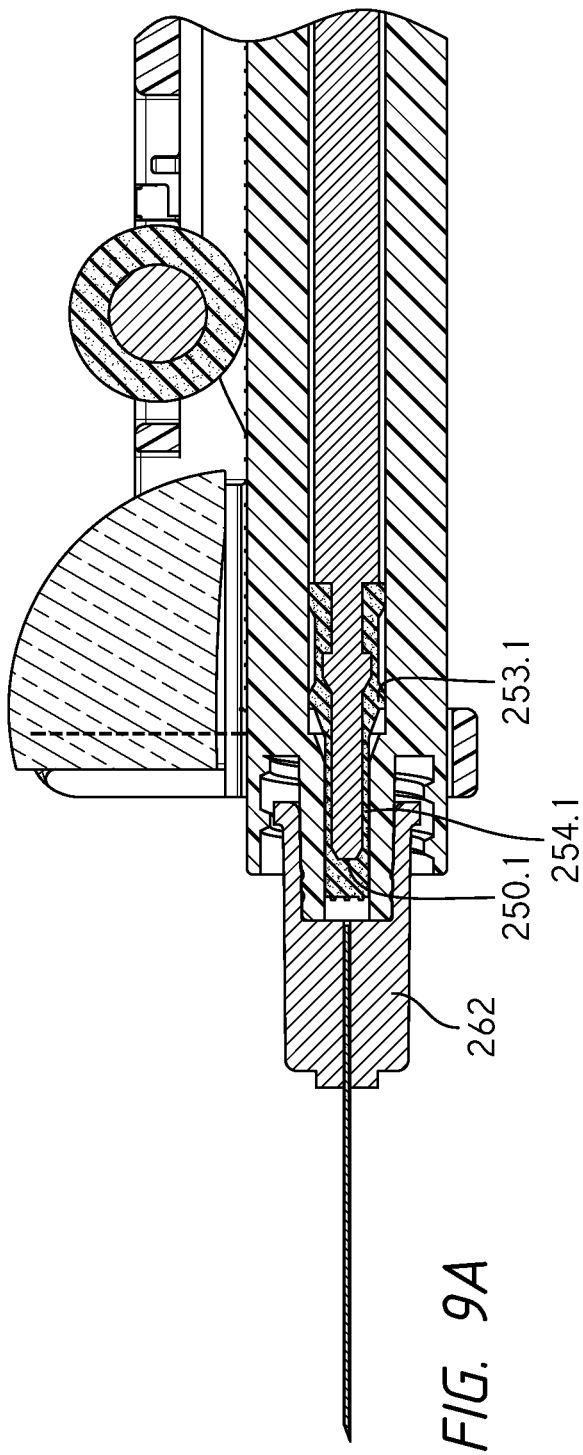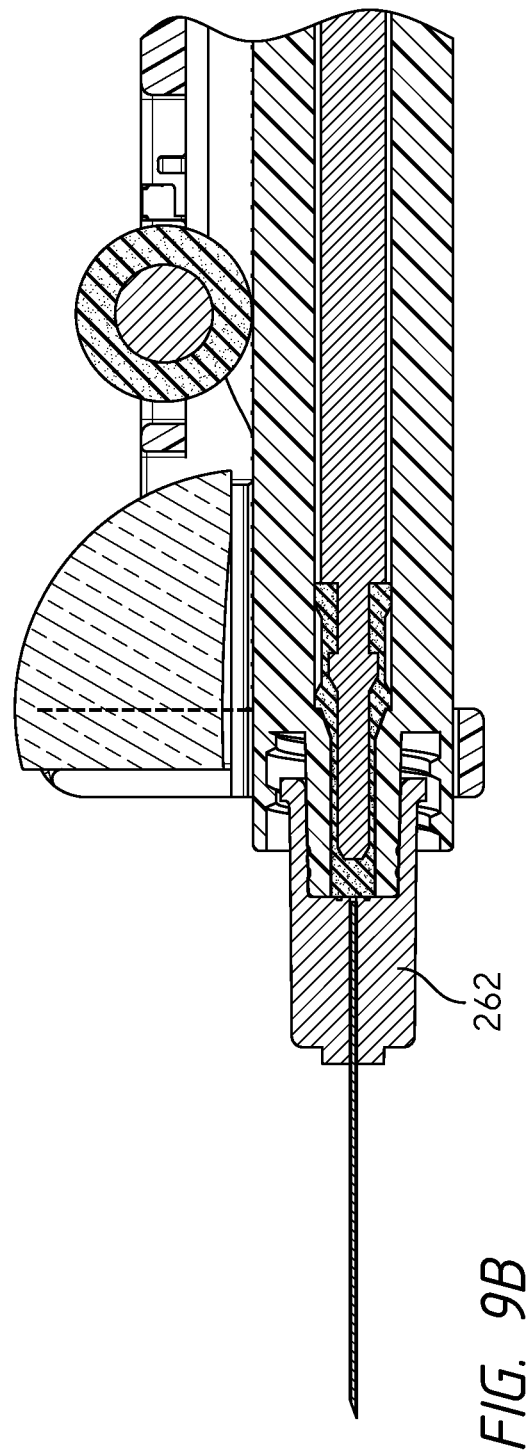
FIG. 9A
FIG. 9B

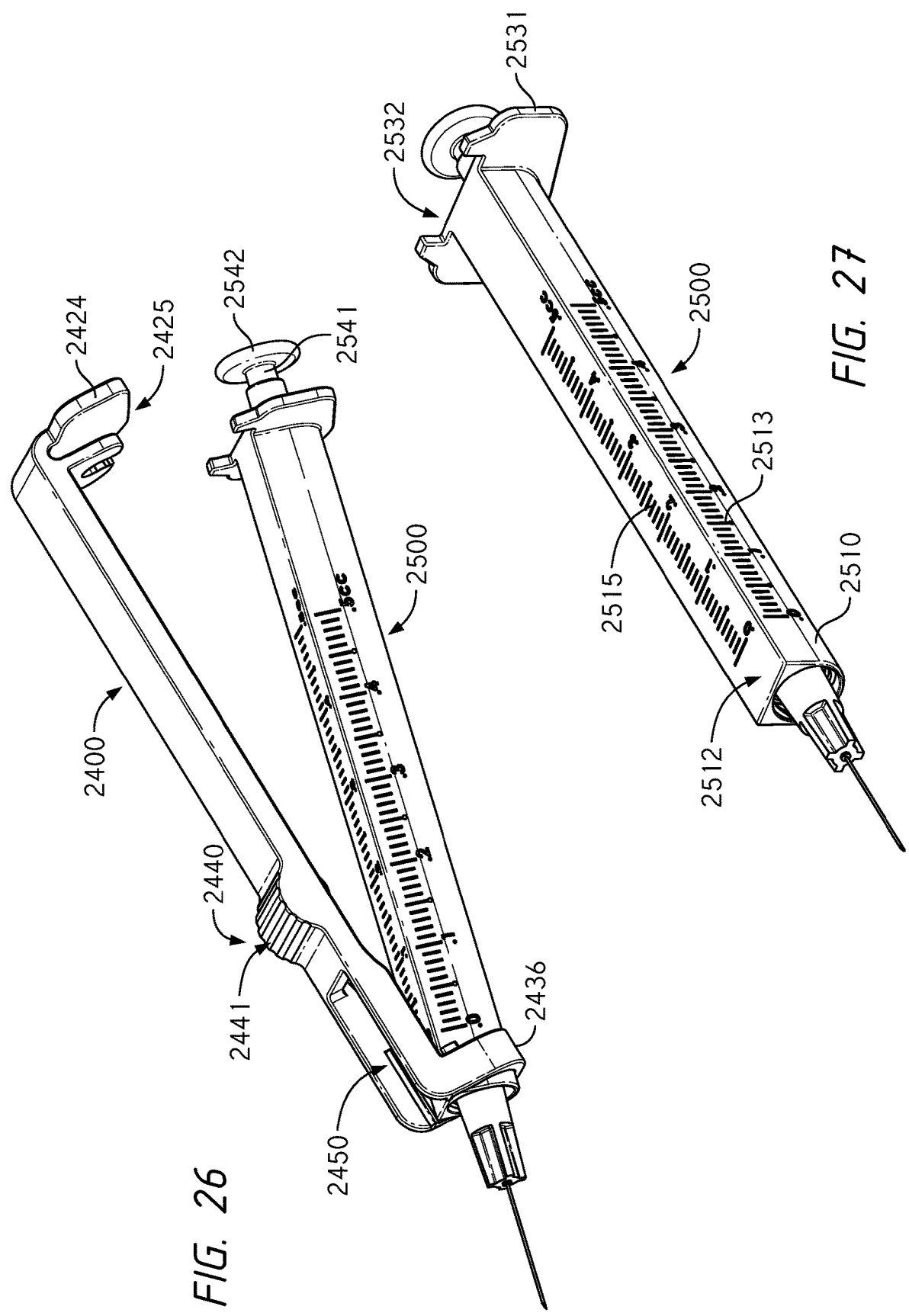

PRECISION LOW-DOSE, LOW-WASTE SYRINGES AND ERGONOMIC ATTACHMENTS THEREFOR

CROSS-REFERENCE TO RELATED APPLICATIONS

This application is a continuation-in-part of, and claims the priority benefit of U.S. application Ser. No. 16/120,122, filed on Aug. 31, 2018, titled PRECISION LOW-DOSE, LOW-WASTE SYRINGES AND ERGONOMIC ATTACHMENTS THEREFOR, which claims the priority benefit of provisional application Ser. No. 62/686,915, filed on Jun. 19, 2018, all of which are incorporated herein by reference.

FIELD

The disclosure relates generally to medical devices, including syringes for controlling delivery of medications and biological fluids to a patient. The disclosure also relates to syringe configurations that facilitate precise delivery of very small volumes and/or doses and low waste of syringe contents. The disclosure relates further to attachments and adapters for improving the ergonomics of syringe operation and for enabling a user to precisely control the actuation of a syringe.

BACKGROUND

In some areas of medicine, there is trend towards lower volume, higher concentration dosages of therapeutic compounds and drugs to be delivered via injection, typically by syringe. For example, in the cosmetic surgery field, recent trends include procedures termed "High Dose Micro-focused" or "HDMF" injections of botulinum toxin, which may involve the use of high concentration and relatively small delivered volumes of compounds or mixtures compared to the concentrations and volumes that have, in the past, been typically used for such injections in cosmetic treatments and in very precise amounts and in very focused, localized areas of the human face and body. The cost of these compounds and mixtures are relatively high to begin with. As the concentrations increase, the relative cost of wasted amounts of the compounds and mixtures also increases.

A number of problems in the prior art stem from the limitations of existing syringes to be adapted to precision, low dose/volume applications. For example, the ability to deliver precise volumes in increments of as small as 0.01 ml may typically be required in such applications. Existing syringe configurations are not readily adapted to precise control of delivery such small increments. A related problem is accurate control and reading of syringes as the form factor becomes reduced. Still another problem is that prior art syringe configurations may demonstrate structural deficiencies when their form factor is reduced. More specifically, for example, reducing the plunger diameter significantly to fit within a reduced syringe lumen may render the plunger susceptible to buckling or bending when a force is applied, thus affecting syringe function and accuracy. Ergonomic factors, including user comfort and control and readability of syringe indicia and plunger position also become a factor as the lumen diameter and other parameters are reduced.

Yet another problem is the need to reduce wasted residual amounts left undelivered in the "dead space" of prior art syringes, as the concentration of expensive substances, such as botulinum toxin in a delivery medium (solvent) increases, the cost of wasted amounts of the mixture also increases.

Another problem relates to the structural shortcomings of traditional syringes when their form factor is reduced in size.

Yet another problem is the need for precise control of the dispensing of syringe contents, such as dermal fillers and other compositions that may be of a relatively high viscosity.

It would therefore be advantageous to provide devices, including syringes and attachments that address the aforementioned shortcoming and others in the prior art.

SUMMARY

According to one aspect of the disclosure, precision low-dose, low-waste syringe configurations are provided for facilitating precise control and delivery of syringe contents and for reducing or eliminating residual waste. The syringe configurations may have a reduced diameter lumen such that a relatively long travel of the syringe plunger is undertaken for dispensing a given volume of syringe contents, which improves the precision with which contents can be dispensed. Total syringe volume may be on the order of 0.25 or 0.50 milliliters.

According to another aspect of the disclosure, an ergonomic attachment is provided for improving the control and precision of delivery of syringes. The attachment may be used with syringes such as the low-dose, low-waste syringes described herein, or may be used with known traditional prior art syringes to improve the precision and control thereof. A main body extends axially to a plunger engaging end and a syringe guide end. The plunger engaging end may include a receptacle for receiving a thumb pad on the end of the syringe plunger. The guide end includes a guide, which provides for sliding engagement with the syringe barrel. The main body includes a gripping surface to permit a user to engage the attachment with his or her fingers or thumb and to move the attachment main body, and thus the syringe plunger, relative to the syringe barrel using sliding movement between the user's thumb and fingers. This mode of actuation provides improved control of the syringe, enables the user to grip the syringe closer to the injection point (needle end), provides stability to the syringe plunger, and provides more accurate control of the delivery of syringe contents.

According to a further aspect, a syringe attachment is provided with an assist feature, which may be a traction wheel mounted on the attachment body. The traction wheel may provide a mechanical advantage, i.e., leverage, to enable the user to move the attachment body, and thus the syringe plunger, with high precision. A number of wheel mounting slots may be provided on the attachment body to enable a user to select a comfortable position. The attachment may be provided as a kit including a number of wheels of various sizes to enable a user to configure the attachment according to their preference for comfort and control. The wheel may be mounted for selective engagement with the syringe barrel. In one configuration, the main body may flex to permit the wheel to engage the syringe barrel when pressure is applied by the user's thumb. In another configuration, the wheel may be biased in an unengaged position using springs or resilient elements in the mounting slots.

According to another aspect, an attachment is provided with features for generating tactile indications to a user of a precise incremental dose. A syringe body may be provided with raised gradations formed therein and on a surface that is engaged by an assist feature on the attachment. When the assist feature is rolled over each raised portion, the user senses the tactile event and perceives that the syringe plunger has moved one increment. Thus, more precise indication and control is facilitated for even small movements of the syringe plunger.

According to another aspect, optical enhancement features are provided to improve the readability of gradations and plunger position. Small gradations indicating incremental doses of as small as 0.01 ml may be provided on the syringe barrel. A magnifying element, such as a prism or lens, may be incorporated into the attachment near the syringe guide end. A reference sight, which may be hairline indicator incorporated into the attachment and/or magnifying element, may be provided on the attachment guide end to indicate the position of the attachment, and thus the plunger and plunger end, relative to the gradations on the syringe barrel. In this manner, very fine gradations may be indicated on the syringe barrel and can be read in combination with the plunger position to indicate very small incremental movements of the plunger.

According to a further aspect, syringes are provided which have particular suitability to low dosage applications. Overall syringe volumes of 0.25 ml or 0.50 ml require small lumen diameters and small plunger diameters. The syringe barrel may be provided with gradations corresponding to 0.01 ml incremental doses, resulting in 25 gradations on the 0.25 ml configuration and 50 gradations on the 0.50 ml syringe. The syringes may be provided with a thickened wall to facilitate handling and control. A flat portion on the syringe barrel improves the readability of the gradations and viewing of the syringe contents and plunger piston as well as operation with optical enhancements on an attachment that may contain an assist feature that facilitates precise control of the plunger movement.

According to another aspect, syringe plunger configurations and needle hub/syringe interfaces with eliminated dead space. A lumen end wall extends into abutting engagement with an end surface of a needle hub. The plunger piston is provided with a flat surface such that the lumen is entire evacuated when the plunger is in its fully inserted position and no waste material remains except in the small needle lumen. This results in cost savings.

According to another aspect, syringe attachments and syringes are provided which have particular suitability to the precision dispensing of small amounts of high viscosity materials, such as dermal fillers. A syringe may include a generally rounded barrel with a flat upper surface and pair of lateral toothed elements, such as racks extending in an axial direction. An attachment may include a main body having a syringe plunger engaging end for engaging and retaining the syringe plunger, and a guide end opposite the plunger engaging end for receiving and slidably guiding the attachment main body along the syringe body. A rolling element may include a wheel with an outer traction or gripping surface and axle rotatably mounted in a pair of journals extending from the attachment main body. The rolling element may include pinion gears on each side of the wheel which engage respective ones of the racks. The pitch diameter of the pinion gears may be less than the diameter of the wheel outer gripping surface such that a mechanical advantage is provided to the user as the wheel and pinions are rotated relative to the syringe body and racks, thus allowing the user to move the carriage in a precise manner relative to the syringe body using the rolling element. Guide elements on the attachment main body and guide end provide smooth operation.

According to another aspect, syringe attachments and syringes may include precision position indicators viewed from multiple positions to enable a user to determine plunger position and the amount of dispensed contents with precision. Indicia may be provided on both the flat upper surface of the syringe body and on the sides of the syringe body. The attachment body may have a viewing window with a sight line or reticle which permits the user to precisely determine the attachment position relative to the syringe. The syringe body may include a transparent or translucent material that allows viewing of the syringe plunger thru the syringe body and the viewing window from a top position. The attachment may also have lateral position indicators that indicate the attachment position relative to the indicia on the sides of the syringe body and thus allow a user control the amount of dispensed contents by viewing from a lateral position.

According to another aspect, an attachment and attachment/syringe combination may utilize an attachment that may be slidably secured to a syringe to permit a user to operation the syringe from a lateral position using sliding movement of the thumb and fingers of one hand, for example. This configuration may be particularly suitable for self-administered insulin injections in extremities (i.e., arms or legs) of the human body where single hand operation of a traditional syringe (thumb on the plunger button) does not facilitate precise dispensing of syringe contents.

DESCRIPTION OF THE DRAWINGS

The above and other attendant advantages and features of the invention will be apparent from the following detailed description together with the accompanying drawings, in which like reference numerals represent like elements throughout. It will be understood that the description and embodiments are intended as illustrative examples according to aspects of the disclosure and are not intended to be limiting to the scope of invention, which is set forth in the claims appended hereto.

FIG. 2A is an exploded view of the attachment and syringe combination of FIG. 1. FIG. 2B is a detail view of a portion of FIG. 2A as indicated.

FIGS. 8A and 8B are cross-sections showing an example needle hub/syringe interface and plunger seal advantageous for a syringe having a total volume of about 0.25 ml, with the plunger in a slightly open position and a fully inserted position, respectively.

FIGS. 9A and 9B are cross-sections showing an example needle hub/syringe interface and plunger seal advantageous for a syringe having a total volume of about 0.50 ml, with the plunger in a slightly open position and a fully inserted position, respectively.

FIG. 26 is a perspective view showing an installation step of the attachment shown in FIG. 24

FIG. 27 is a perspective view of a syringe according to aspects of the disclosure.

DETAILED DESCRIPTION

The terms "cooperate," "cooperatively" and "cooperating" as used herein are intended to imply an operational relationship between elements, for example, such that motion of one element results in relative motion of the other element, either directly, or indirectly thru one or more intermediate elements. Thus, a gear or pinion cooperating with a rack may include intermediate gears or other elements for causing or transmitting relative motion between the gear and the rack. The term "adapted to" as used herein means that an element or component includes structure which may operate or be operated to achieve a specified result to which the element is adapted.

Figure 1:
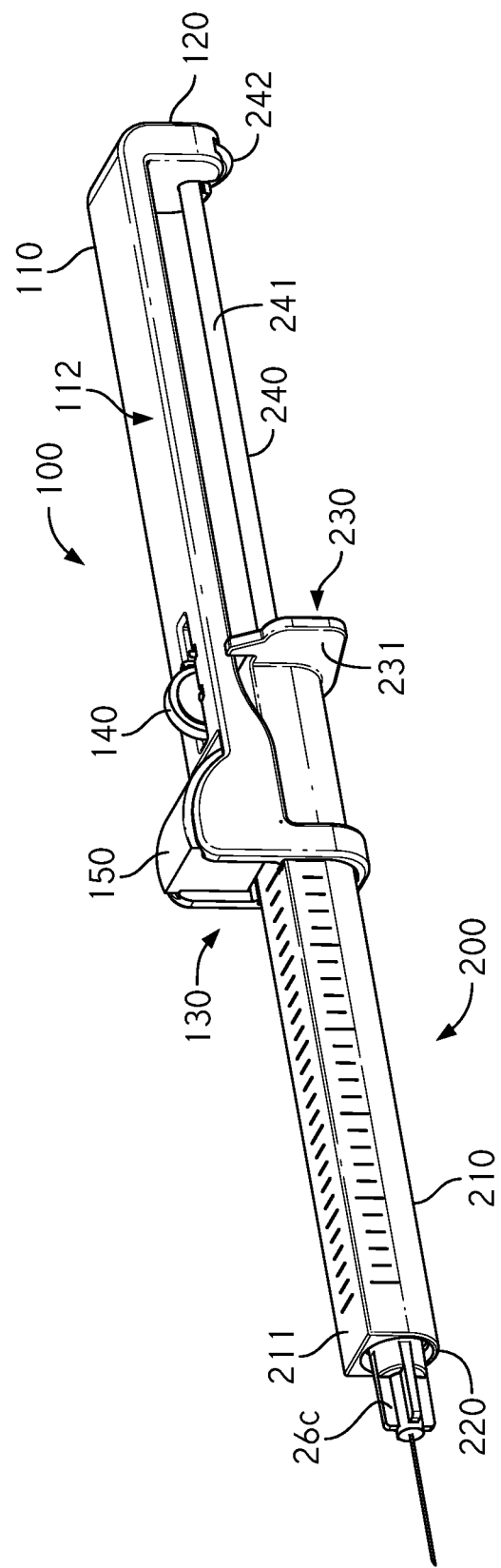
FIG. 1 is a perspective view of an example attachment, according to aspects of the disclosure, assembled on a syringe, according to aspects of the disclosure.
Figure 5:
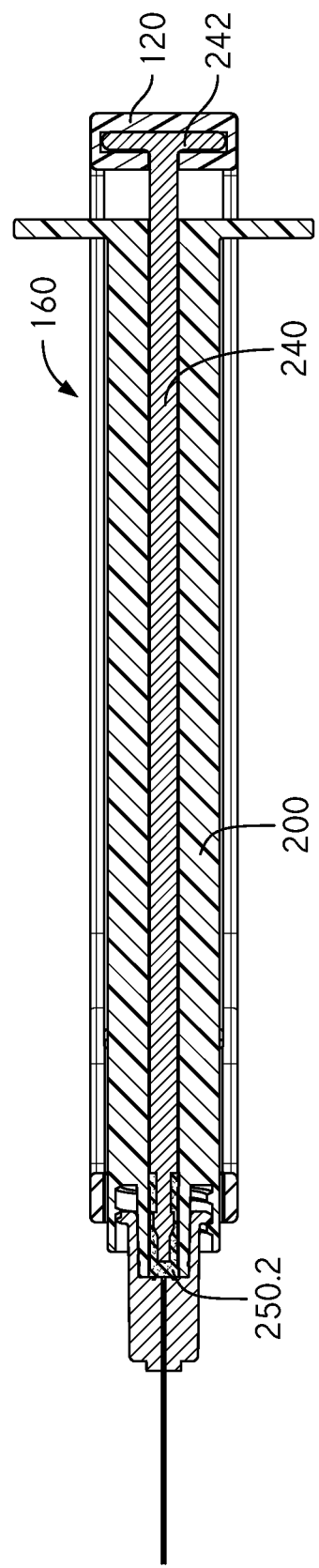
FIG. 5 is a cross-section of the attachment and syringe combination of FIG. 3 in the plane 5-5 in FIG. 3.

FIGS. 1 and 2A show an assembled view and an exploded view, respectively, of an example syringe attachment 100 and syringe 200 according to aspects of the disclosure. Attachment 100 may include an elongate main body portion 110, which extends from a syringe plunger engaging end 120 to an opposite syringe guide end 130. Main body portion may include a gripping surface 112 which permits a user to apply a sliding force on the attachment using the fingers and or thumb. Syringe plunger engaging end 120 may include a receptacle or slot 122 for receiving a thumb pad or button 242 of the syringe plunger. An aperture 124 may accommodate the plunger shaft 241. Receptacle 122 and/or aperture 124 may be sized to provide a friction fit around thumb pad 242 and plunger shaft 241 to firmly retain the plunger relative to the attachment 100. FIG. 5 is a cross section that further illustrates an example orientation of the syringe button 242 within the syringe plunger engaging end 120 of attachment. Syringe guide end 130 may include a generally U-shaped syringe guide 135 that is shaped complementarily to the outer surface of the syringe barrel 210 and includes an inner surface 136 that facilitates sliding movement along the syringe barrel 210. Surface 136 may be provided with a friction reducing coating, lubricant or surface texture. A pair of opposed retaining edges 138 may be formed in the guide end 130 to engage a flat portion of the syringe barrel to keep the attachment aligned with the syringe barrel (and plunger) axis and prevent lateral and upward movement of the syringe barrel 210 within the guide 135.

According to aspects of the disclosure, syringe 200 includes features for facilitating the storage and delivery of very small incremental doses, including with a small diameter lumen, plunger diameter and plunger seal, while having an external form, i.e., outside diameter that facilitates easy handling. In this regard the barrel walls may be of increased thickness compared to prior art syringe configurations. Syringe barrel 210 may be provided with an internal lumen diameter that provides a total syringe volume of about 0.50 ml, with 50 gradations indicated on the syringe barrel, or in another configuration, about 0.25 ml, with 25 gradations indicated on the syringe barrel. With a syringe length of 4 inches with a 0.50 ml volume and 50 gradations, for example, each incremental 0.01 ml dose may require a controlled a plunger movement on the order of 0.08 inches. As will be appreciated by those of ordinary skill, the features of the syringe and attachments described above and further below herein will facilitate the small, precise and controlled movements of the syringe plunger for such small incremental doses.

Still referring to FIGS. 1 and 2A, syringe 200 may include a plunger receiving end 230 having a flange 231 extending therefrom, for permitting traditional operation of the syringe 200 using two fingers, one on each side of flange 231, and the thumb on syringe thumb pad 242. The flange 231 may include a recessed portion 232 to accommodate the width of attachment 100. The syringe wall thickness and material are chosen to provide a view of the syringe plunger piston 250.1 within the lumen as viewed thru the flat portion 211 of the syringe barrel 200. A needle receiving end 220 of the syringe may engage a needle hub 260 in a manner that will be described later herein.

Figure 3:
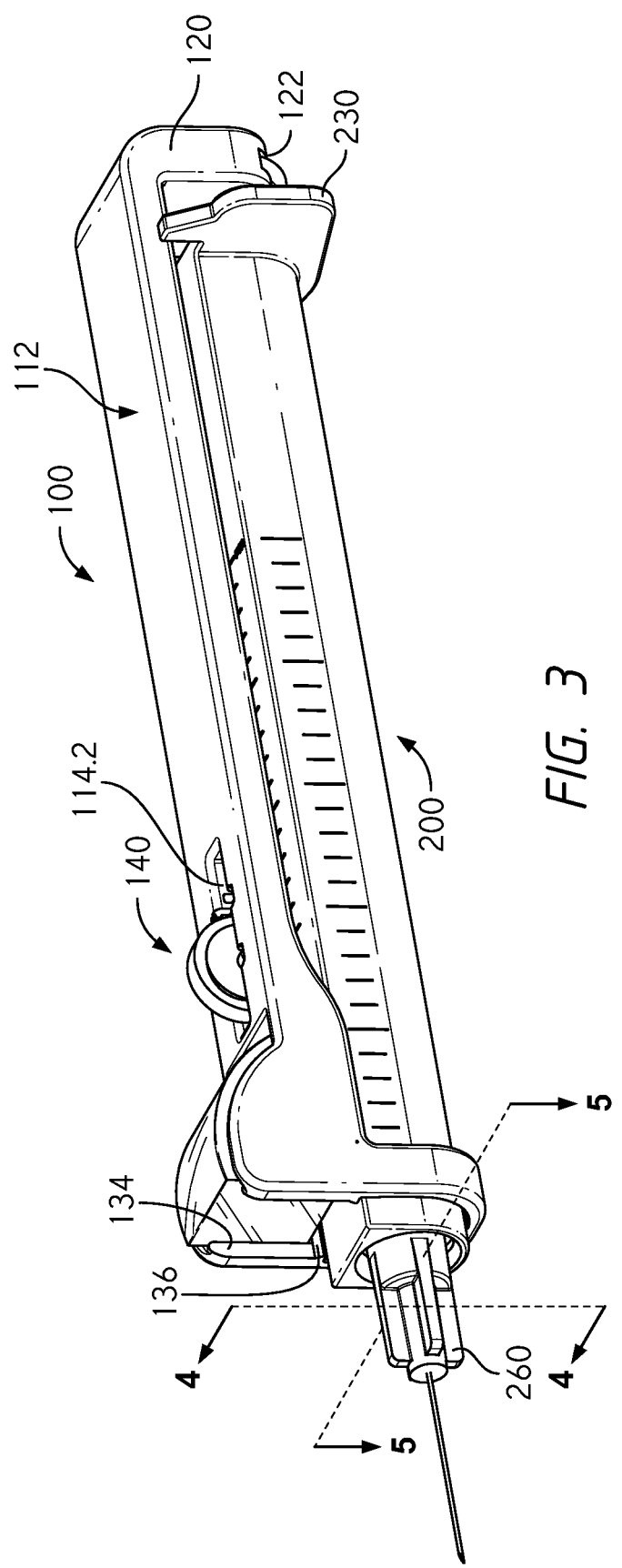
FIG. 3 is a perspective view of the attachment and syringe combination of FIG. 1, showing a different position of the attachment and syringe plunger.
Figure 4:
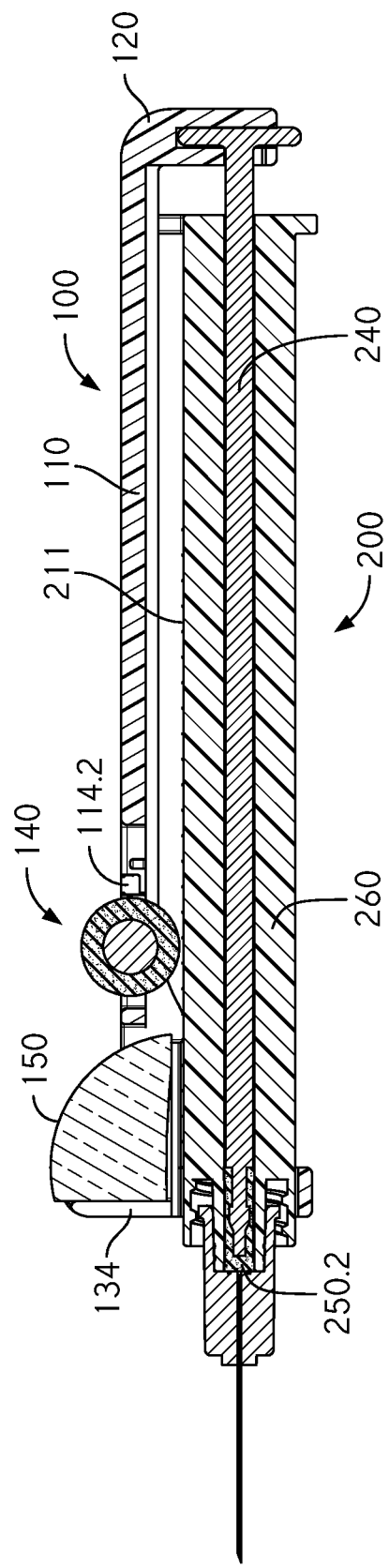
FIG. 4. is a cross-section of the attachment and syringe combination of FIG. 3 in the plane 4-4 in FIG. 3.

According to another aspect of the disclosure, the attachment 100 may be provided with an assist feature 140 to enhance control of the movement of attachment 100, and thus movement of the syringe plunger 241 and piston 250.1 relative to the syringe barrel 200. Assist feature 140 may be provided in the form of a traction wheel, which may include a rubberized outer member 142 mounted on an inner hub 144. Hub 144 may include extending axles that are received in slots 114.1 and 114.2 in the attachment main body 110. Assist feature 140 may provide a mechanical advantage or leverage to the user during operation. More specifically, the user may use their thumb and or finger to rotate the assist feature 140 which may selectively and frictionally engage the flat surface 211 of the syringe body 200. The diameter of the assist feature 140 provides leverage to the user and allows the user to move the attachment incrementally using a rolling motion. Referring additionally to FIG. 4, the assist feature 140 may rest in a disengaged position shown, where it is slightly above and disengaged from the syringe flat surface 211. Selective engagement of the assist feature 140 may be provided by flexibility (deformation) of the main body 110 of the attachment 100. Alternatively, springs or biasing elements may be incorporated into the axles of hub 144 or into the slots 114.1 and 114.2 such that the assist feature 140 engages the surface 211 when a slight downward force is exerted on the assist feature 140 by the user, and disengages the surface 211 when user force is removed. FIG. 3 illustrates the operation of an example syringe/attachment combination and shows a position in which the syringe plunger is fully inserted into the syringe lumen.

According to a further aspect of the disclosure, the attachment and/or syringe may be provided with features that facilitate the tactile sensing of an incremental dose and movement of the syringe plunger. For example, referring to FIG. 2B, the gradation indicia 212 on the syringe barrel flat surface 211 may be provided as raised elements, such as ridges or hashes formed in the syringe barrel and of a suitable dimension such that rolling of the assist feature 140 over each ridge generates a tactile event, such as a slight resistance and/or clicking sound, that can be sensed by the user. As an alternative, assist feature wheel hub 144 may be provided with a sound generator, such as a toothed element and a reed element, that generates a clicking sound for an incremental rotation corresponding to one gradation on the syringe surface.

Figure 6:
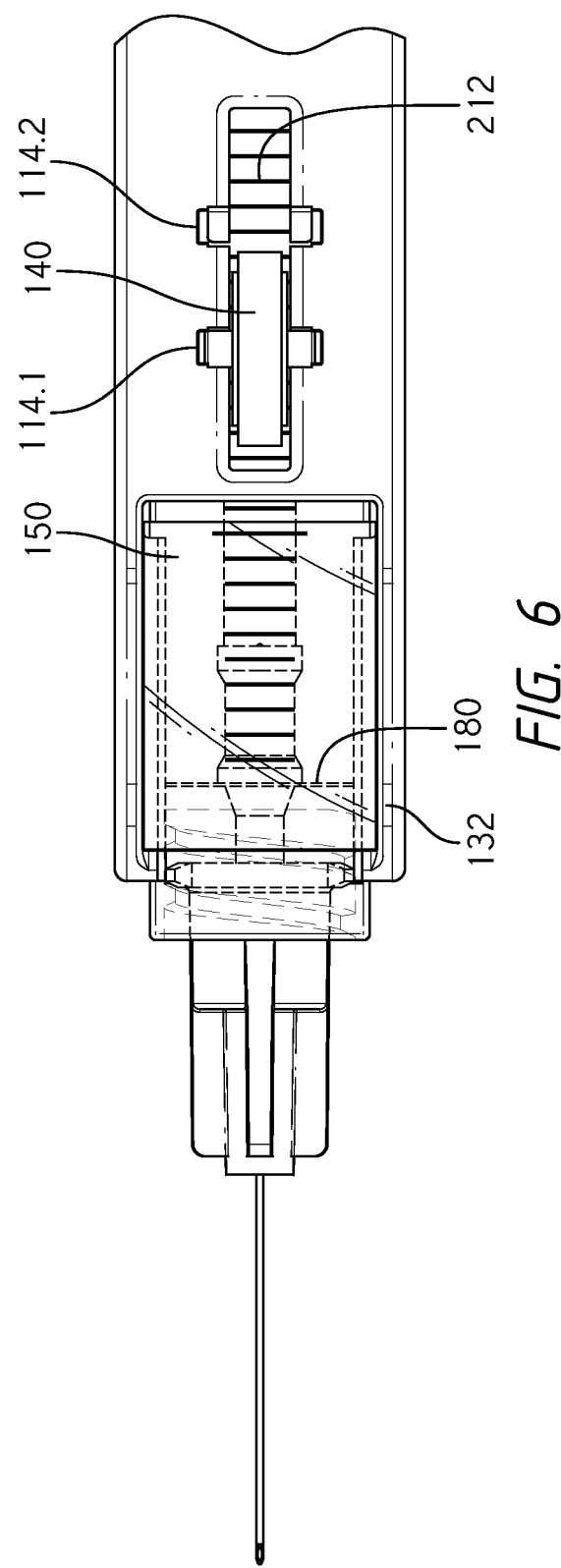
FIG. 6 is a top view of a portion of the attachment and syringe combination of FIG. 3, showing a magnified view thru an optical element.

Referring additionally to FIG. 6, in accordance with another aspect of the disclosure, attachment 100 may be provided with an optical element 150 to enhance the user's viewing of the syringe plunger piston 250.1 and gradations 212 and thus enhance precision of operation of the syringe. Attachment syringe guide end 130 may include a pair of upwardly extending sidewalls 132, each having a vertical shoulder 134 and lower horizontal shoulder 136 which define a receiving space for the optical element 150. Optical element 150 may be a magnifying prism made of an optically transparent material and having magnification properties. As will be recognized, the optical element 150 moves with the syringe plunger and thus stays oriented above the syringe plunger piston 250.1 as the attachment and plunger move during syringe operation, thus enabling the user to see a magnified view of the plunger piston 250.1 and gradations 212 as syringe contents are dispensed/administered. A reference sight line or reticle 180 may be a hairline element incorporated into or adjacent to the optical element or in the attachment and may provide a precise indication of the syringe plunger piston movement, even in cases where the piston is not entirely visible to the user due to syringe wall thickness or material, for example. As best seen in FIGS. 3 and 4, a flat bottom surface of optical element 150 rests a small distance above the flat surface 211 of the syringe barrel. As will be recognized, this distance enables an accurate reading of the syringe gradations and plunger movement. Moreover, this distance may be adjusted/selected in order to vary the level of magnification provided by the optical element.

According to yet another aspect of the disclosure, the assist feature and optical enhancement features of the attachment and attachment/syringe combinations contemplated herein include highly customizable aspects. Attachment 100 may include two or more mounting slots 114.1 and 114.2 to permit a user to customize the assist feature position and thus the attachment configuration according to a desired comfort level. In addition, assist features 140 may be provided as a kit of several different sized wheels with the attachment to enable the user to select a desired wheel size to achieve precise control for the user's hand, finger or thumb size or other attribute. Likewise, the optical element 150 is removable and may be fastened with snap elements/detents onto the attachment 100 and a kit of optical elements of various magnification power may be provided to enable customization according to a user's preferences, or the optical element may be removed to permit a user/physician to use an eye loop or magnifying eyeglasses in conjunction with use of the syringe. As will be recognized, the mounting configuration for the assist feature and the optical enhancement feature permits quick refitting of alternative parts.

Figure 7:
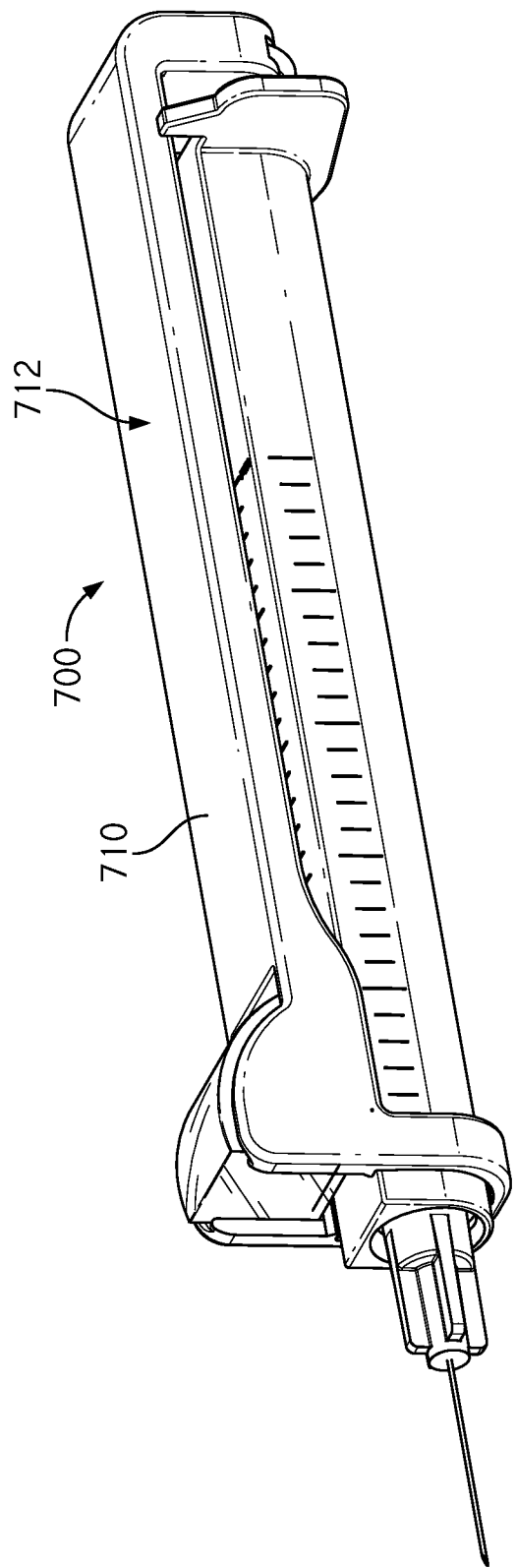
FIG. 7 is a perspective of a first alternative attachment configuration assembled on a syringe, the attachment being without an assist feature.

FIG. 7 illustrates an alternative attachment configuration 700 in which the assist feature is omitted and which facilitates syringe operation using relative lateral (sliding movement) of a user's thumb and fingers. The main body 710 includes a gripping surface 712 to permit a user to engage the attachment with his or her fingers or thumb and to move the attachment main body, and thus the syringe plunger, relative to the syringe barrel using sliding movement between the user's thumb and fingers. This mode of actuation provides improved control of the syringe, enables the user to grip the syringe closer to the injection point (needle end), provides stability to the syringe plunger, and provides more accurate control of the delivery of syringe contents.

According with yet another aspect, the disclosure provides low-waste syringe/needle interfaces and syringe plunger piston configurations. FIGS. 8A and 8B are cross-sections showing an example needle hub/syringe interface and plunger seal advantageous for a syringe having a total volume of about 0.25 ml, with the plunger in a slightly open position and a fully inserted position, respectively. Needle hub 260 includes a needle 262 mounted therein and an end surface 264 with which the end of needle 262 is flush mounted therewith. Needle hub 260 includes an outer threaded base that engages internal threads on the syringe. Syringe 200 includes an internal lumen wall extension 242 that extends into the interior of needle hub 260 and has an end 243 that forms a sealing interface with the hub end surface 264. Syringe plunger piston 250.2 includes an internal space for receiving a barb-like end 245 of plunger 240. Syringe plunger piston 250.2 also includes a flat end surface 252.2. As can be seen with additional reference to FIG. 8B, when the piston is at the full extent of its insert into the syringe lumen, the piston end surface 252.2 is in abutting contact with the end surface 264 of the needle hub, thus eliminating any dead space within the needle hub and thus completely evacuating the syringe contents from the lumen. This may result in significant cost savings for expensive syringe contents. For delivery of syringe contents, needle 262 may be a 30-gauge needle, which is of a small size and mitigates pain and tissue damage during injection. Moreover, one method of operating the device contemplated herein is to utilize a larger (smaller gauge) needle of a standard, low cost configuration, such as a standard 20-gauge needle on the syringe, to facilitate quick retrieval of material (i.e., neurotoxin) into the syringe. Once the syringe is filled, a 30-gauge needle with the low-waste features described herein may be installed on the syringe and used for delivery.

FIGS. 9A and 9B are cross-sections showing an example needle hub/syringe interface and plunger seal advantageous for a syringe having a total volume of about 0.50 ml, with the plunger in a slightly open position and a fully inserted position, respectively. In this configuration, the syringe lumen has an increased diameter compared to the configuration of FIGS. 8A and 8B. The syringe piston 250.1 may include a first portion 253.1 that has a diameter suitable to form a seal with the lumen. The first portion 253.1 may taper down to a smaller diameter portion 254.1 that fits within the interior of the lumen end wall, which may be of a standard dimension to fit a standard needle hub 260.

Figure 10:
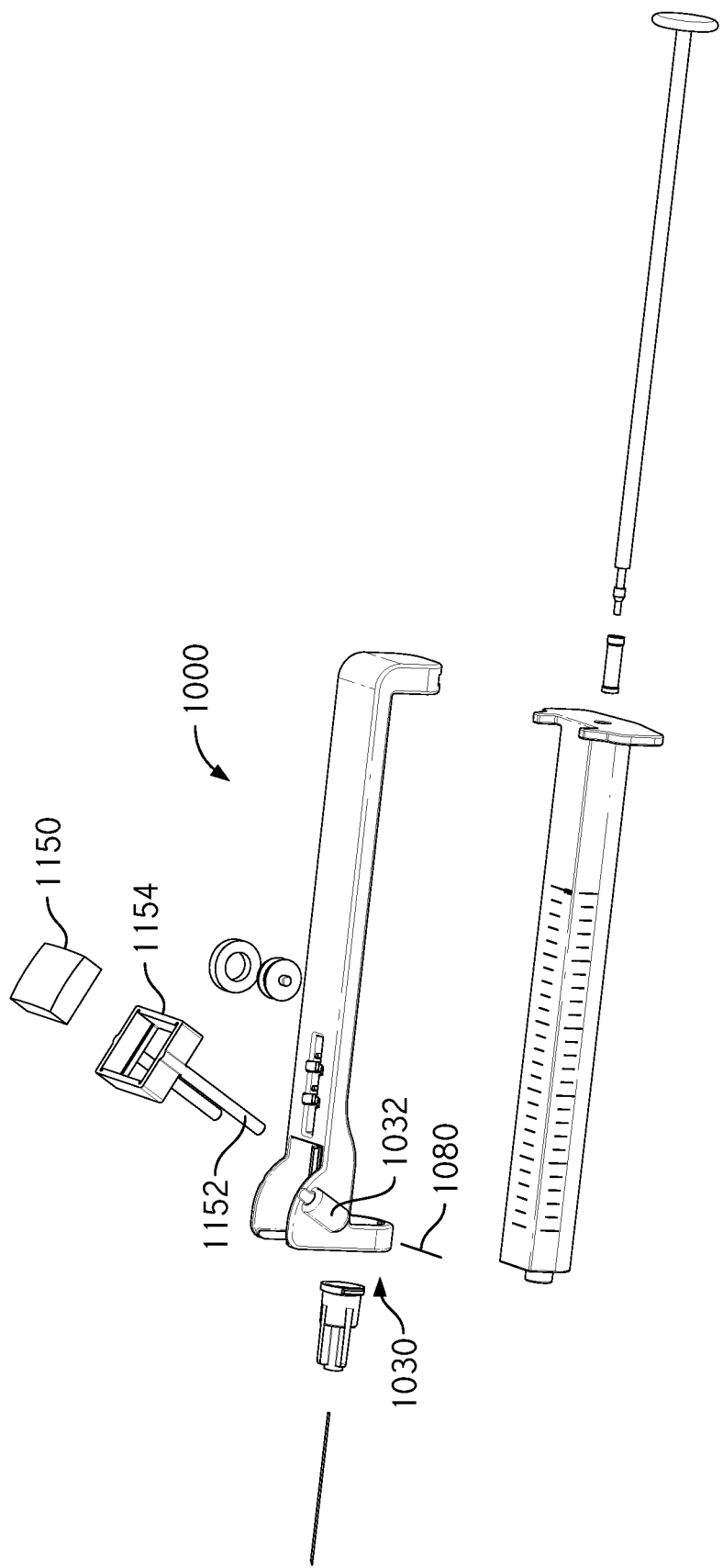
FIG. 10 is an exploded view of an attachment and syringe with the attachment having an optical element mounting component that is adjustable.

FIG. 10 is an exploded view of an alternative attachment configuration 1000 showing an alternative optical element mounting arrangement. Attachment guide end 1030 may include a pair of circular mounting tubes 1032 formed therein (one shown in FIG. 10) which receive respective mounting rods 1152 of a lens mounting frame 1154. A magnifying lens 1150 may be mounted within the lens mounting frame. This configuration may provide higher magnification of the syringe gradations and reference sight 1080 and may be adjusted to a user's preference.

Figure 11:
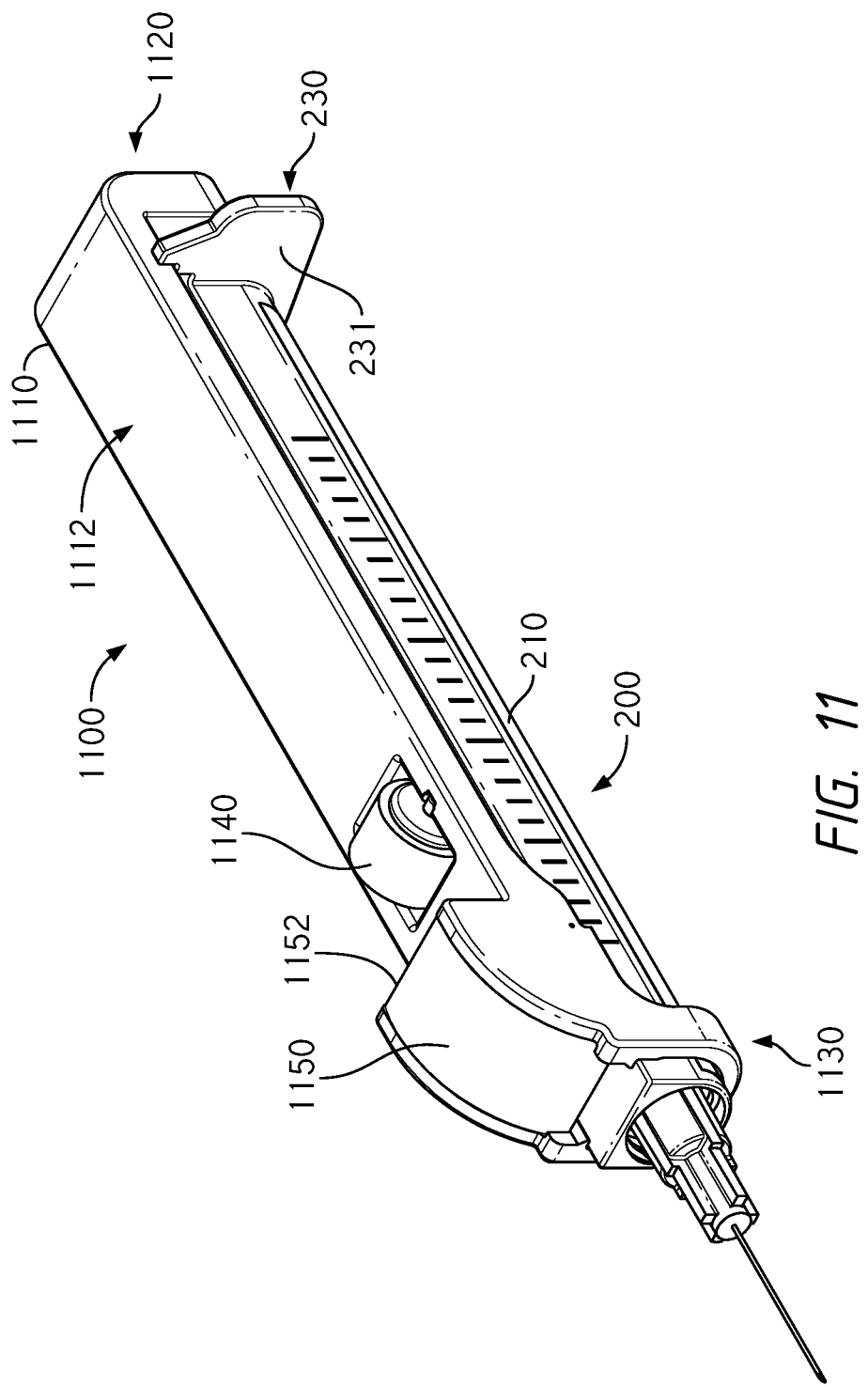
FIG. 11 is a perspective of second alternative attachment configuration assembled on a syringe.
Figure 12:
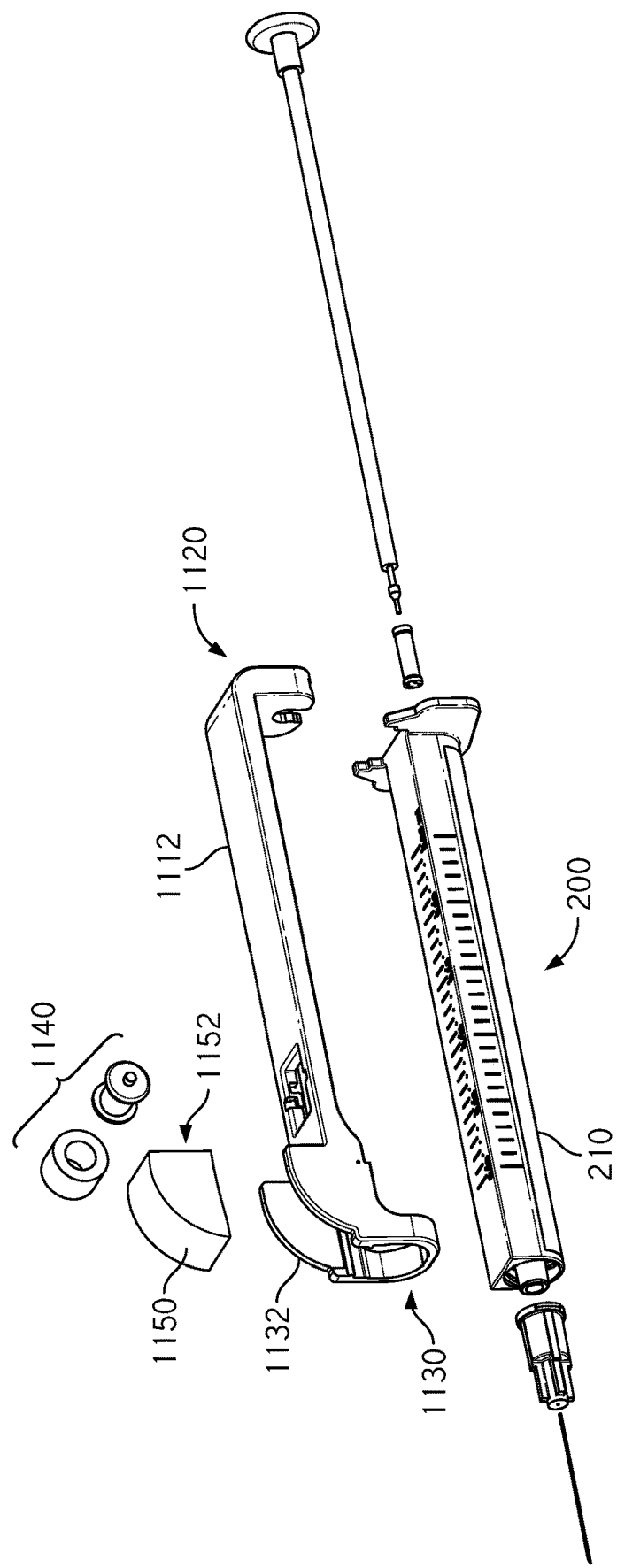
FIG. 12 is an exploded view of the alternative attachment and syringe combination of FIG. 11.
Figure 13:
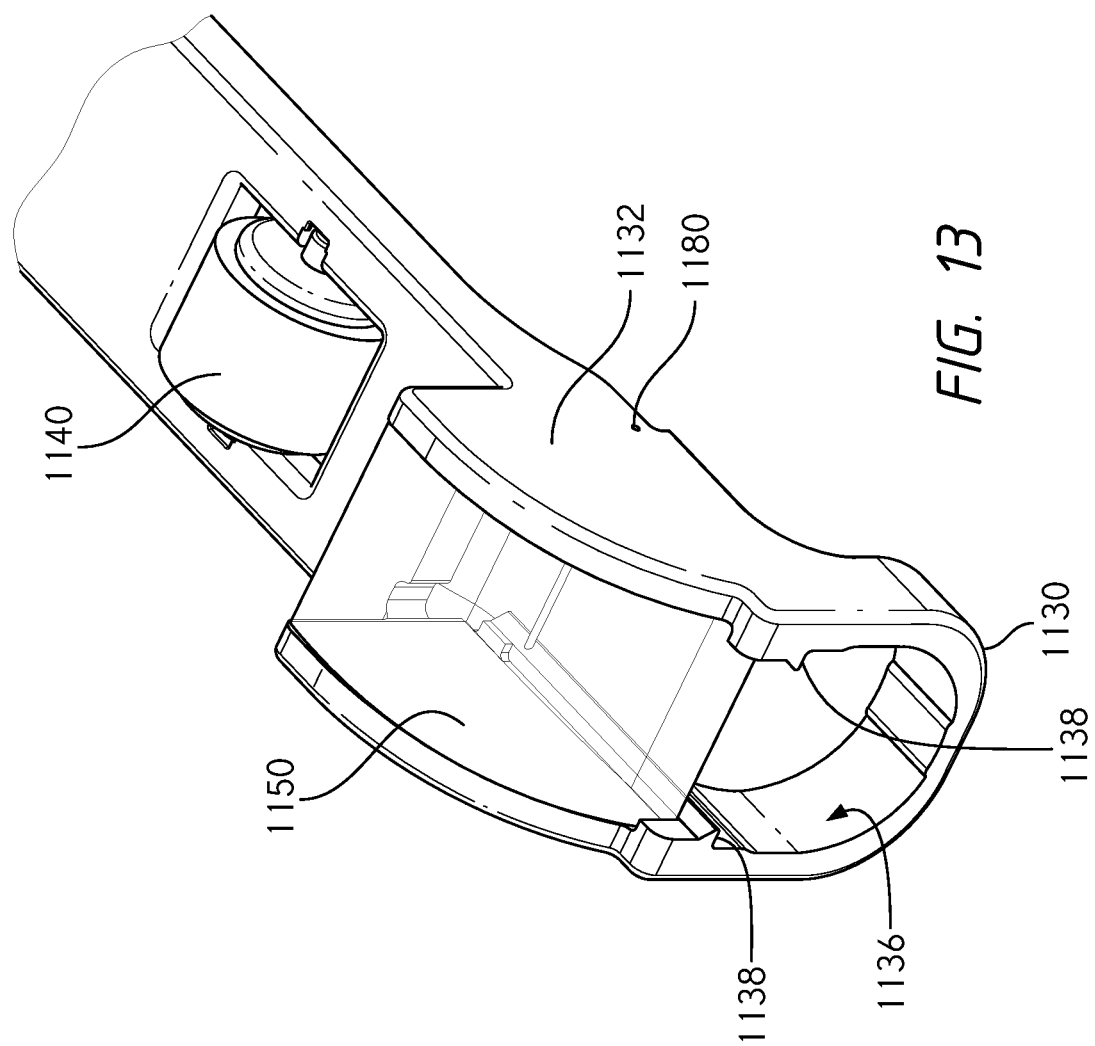
FIG. 13 is a detailed perspective of a syringe guide end of the alternative attachment of FIGS. 11 and 12.

FIG. 11 is a perspective view of an assembled alternative attachment 1100 and syringe 200 according to alternative attachment configuration 1100. FIG. 12 is an exploded view of the same embodiment. In this embodiment, the magnification element 1150 is oriented differently than in the embodiment of FIG. 1, with a flat side 1152 of the magnifying element 1150 facing the assist feature 1140. This configuration provides additional clearance for the user's thumb when engaging the assist feature 1140 and provides a viewing angle of the magnified area of the syringe (the area beneath the magnifying element 1150) that may be ergonomically advantageous, i.e., allowing the user to view the magnified areas of the syringe from a direction towards the needle end of the syringe and closer to the area of focus when performing injections.

Figure 14:
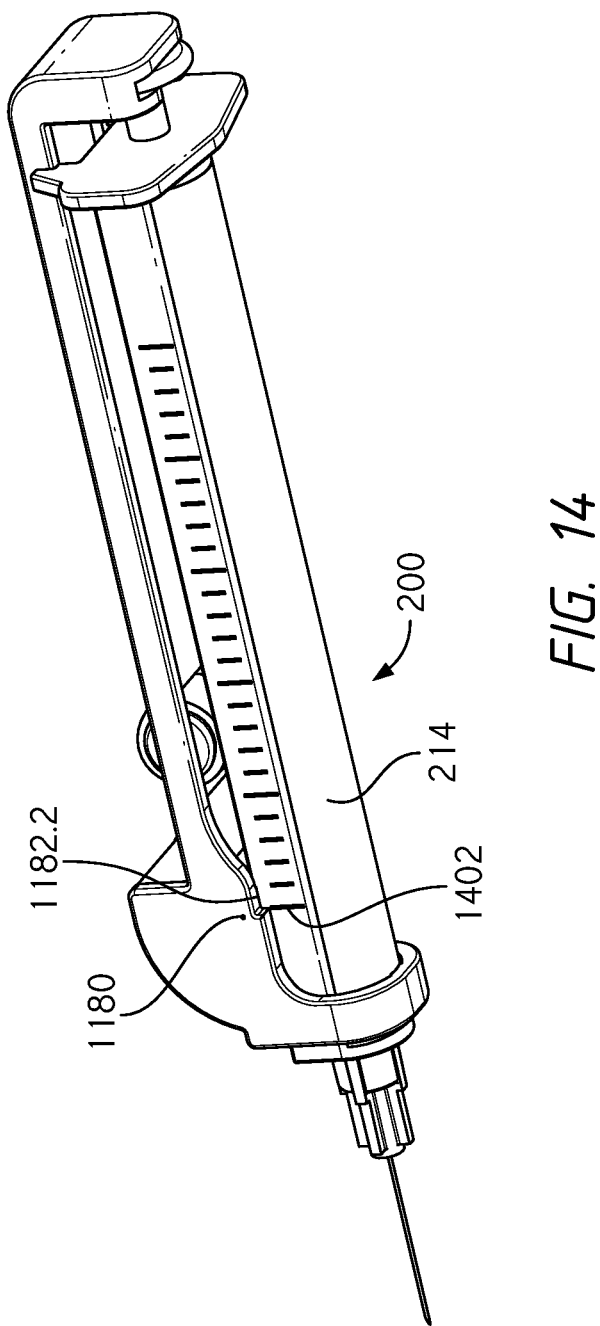
FIG. 14 is a bottom perspective of the attachment and syringe combination of FIG. 11.
Figure 15:
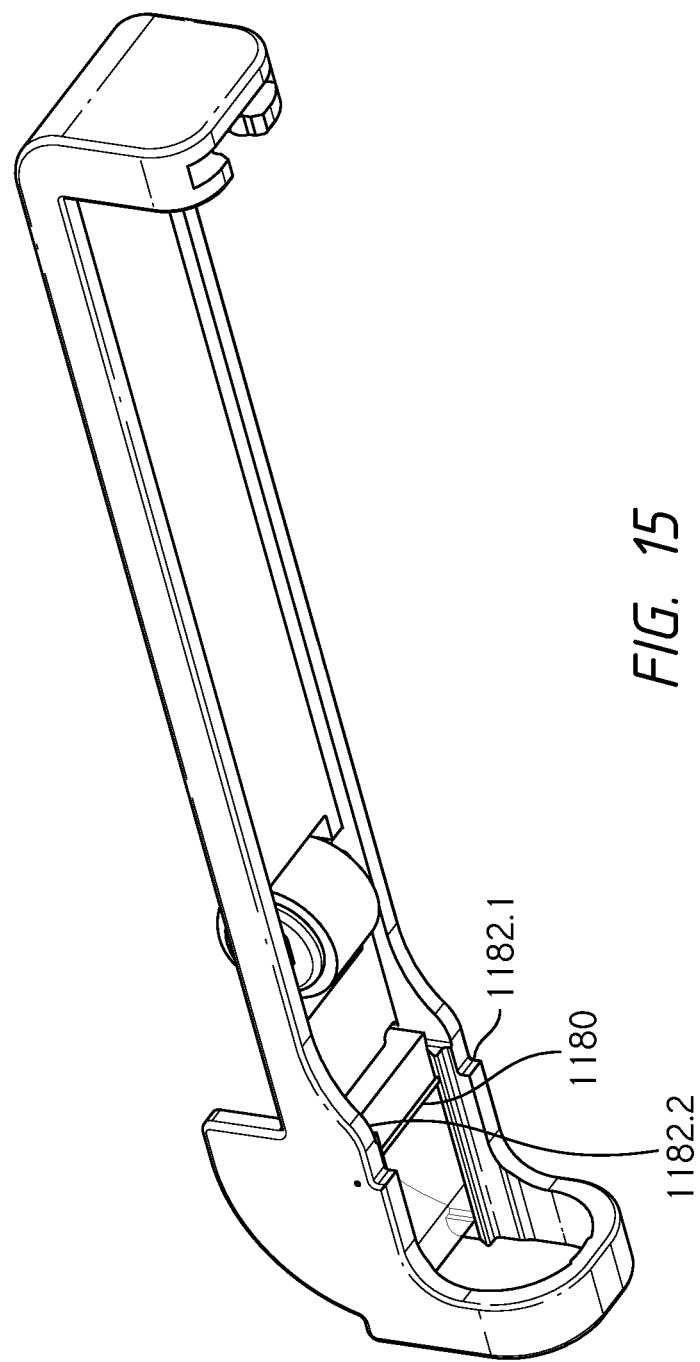
FIG. 15 is a bottom perspective of the attachment of FIG. 11.

FIG. 14 is a bottom perspective view of the attachment/syringe combination of FIG. 11 with the attachment in a "zero" position in which the contents of the syringe have been entirely evacuated. As can be seen, the reference sight line or reticle 1180 coincides with the gradation 1402 representing a "zero" or fully emptied position of the syringe. As will be recognized, the "zero" gradation may be positioned in an offset manner from the zero position of the syringe plunger (i.e., when it is bottomed against the end wall of the lumen) such that the reticle 1180 and zero gradation 1402 can indicate the fully emptied position of the attachment precisely to the user. Referring additionally to FIG. 15, reticle 1180 may include a filament coated with a conspicuous color, such as red, in order to provide a sharp contrast and enable the user to see the precise location of the plunger (and position of the attachment relative to the syringe) when the user views the magnified syringe area within the field of view of the magnifying element 1150. To further enhance viewing and precision, the attachment may include lateral reference shoulders 1182.1 and 1182.2 that coincide with the reference line or reticle 1180 and enable the user to view the position of the reticle 1180 from the sides of the syringe. The reference shoulders 1182.1 and 1182.2 may include a coating in a conspicuous color, such as red, to further define a line of reference on the attachment. As seen in FIG. 14, the reference shoulder 1182.2 is aligned with the "zero" gradation when the syringe plunger, and thus the attachment, have reached the full extent of their travel relative to the syringe.

A bottom surface 214 of the syringe 200 may be provided with an opaque coating that may be of color that results in sharp contrast with the syringe contents and syringe plunger to provide additional ease of viewing by the user of the position of the syringe plunger and the plunger/contents interface (demarcation line). The opaque coating may substantially cover the lower half of the barrel, or may include patterns that enhance the user's viewing of the syringe contents and plunger position. For example, an axially extending break may be provided in the opaque coating directly beneath the lumen where the translucency of the syringe barrel allows light to pass to the interior of the lumen from the syringe barrel underside thereby enhancing the user's viewing of the syringe contents and plunger position.

Figure 16:
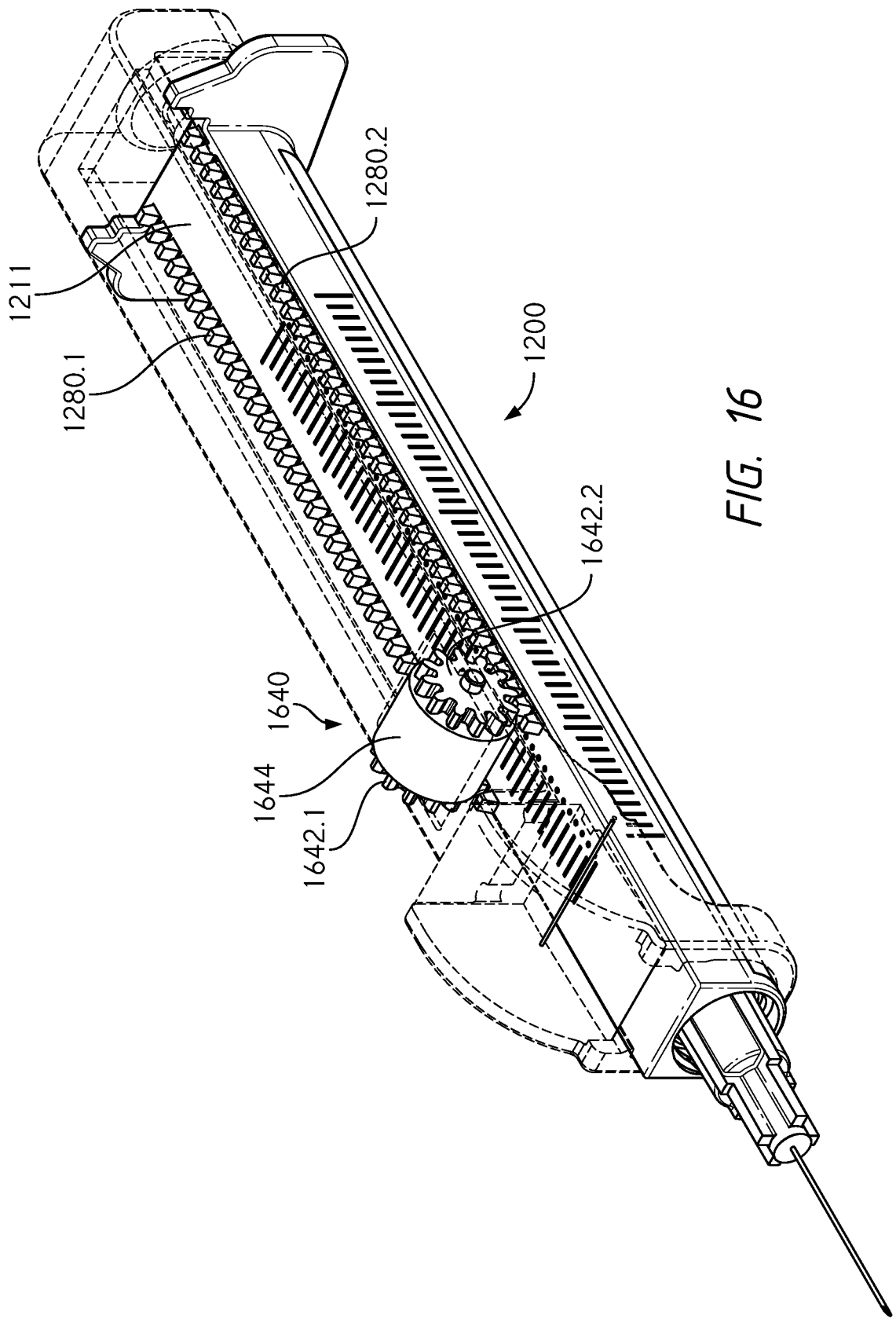
FIG. 16 is a perspective view of a third alternative attachment and syringe combination.
Figure 17:
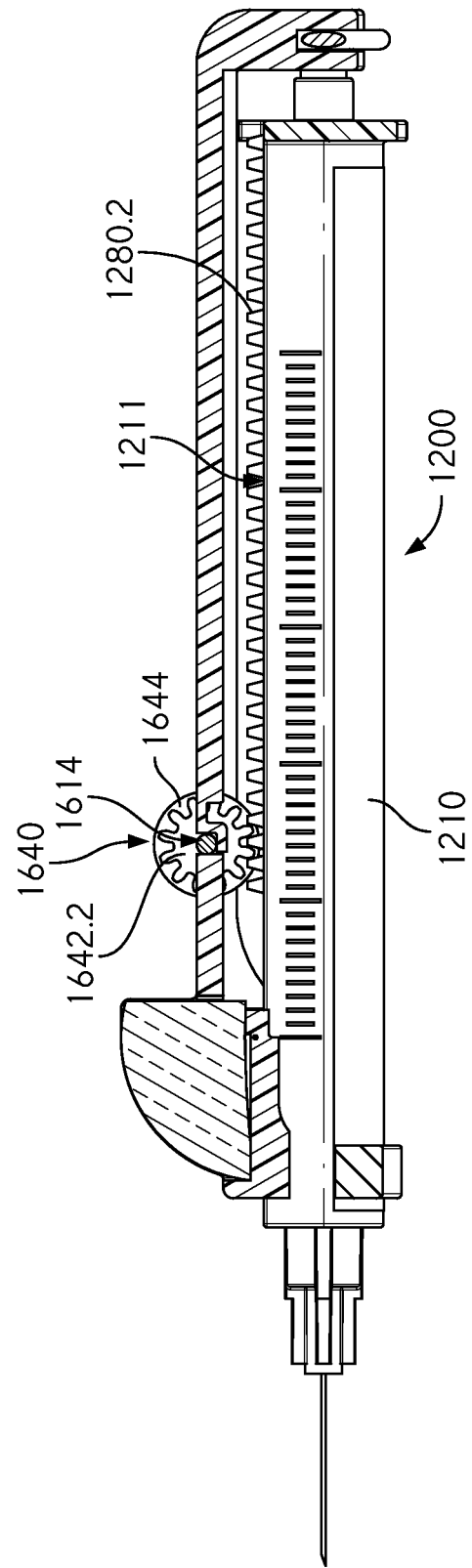
FIG. 17 is a side view of the attachment and syringe combination of FIG. 16.

FIGS. 16 and 17 illustrate another alternative configuration for a syringe attachment and syringe. This configuration may be useful for precision dispensing of more viscous syringe contents, such as dermal fillers. In this configuration, the assist feature 1640 may include one or more toothed elements 1642.1 and 1642.2, such as pinion gears formed on the hub of a circular element, such as a wheel, rotatably mounted in the attachment main body in a manner as described above with regard to elements 142 and 144 in FIGS. 1 and 2A. The pinion gears 1642.1 and 1642.2 cooperate with respective geared rack elements 1280.1 and 1280.2 formed on a flat portion 1211 of the syringe barrel 1210. This configuration, as will be recognized, provides a positive actuation (i.e., no slippage) feature for the syringe attachment relative to the syringe. A rubber gripping surface 1644 may enhance the user's ability to rotate the assist feature 1640. Moreover, the assist feature 1640 may be mounted such that it may be free to rotate (i.e., the pinions are not engaged with the racks) in the absence of lateral pressure (downward in FIG. 16) on the assist feature. This may be accomplished with spring elements supporting the wheel 1644 within the mounting slots 1614 (FIG. 17) on the attachment, or by making the main body of the attachment sufficiently flexible that lateral pressure on the assist feature 1640 causes deformation of the attachment main body and resulting engagement of the pinion gears with the racks. In this manner, inadvertent actuation of the plunger can be avoided. That is, the user must apply lateral pressure to the assist feature before rotating the assist feature in order for syringe contents to be dispensed. The pitch and profiles of the pinion teeth and rack teeth may be designed such that each incremental engagement of a tooth coincides with each gradation on the syringe, or a predetermined volume of dispensed material. Moreover, the profile of the pinion teeth and rack teeth may provide interference, or may include projections or other features that provide tactile and audible feedback to the user, i.e., clicking sensation or sound, which corresponds to a known incremental dispensed volume or to the gradations on the syringe.

FIGS. 18-23 illustrate a syringe and attachment combination that may be particularly suitable for precision and low-waste dispensing of relatively small amounts of high viscosity materials, such as dermal fillers. This combination provides positive control of the syringe attachment, and thus the plunger position relative to the syringe body as well as a mechanical advantage that reduces the force needed to be applied by the user to dispense the high-viscosity contents. Attachment 1800 may include main body 1810 having an upper wall 1811 and two lateral walls 1814, a plunger engaging end 1820 and a guide end 1835 for receiving and facilitating guided movement along a syringe 1900. The main body 1810 may include a viewing window 1850 (see FIGS. 18, 20 and 21) defined therein for viewing the syringe upper surface, indicia thereon, and the syringe plunger end (viewed through the transparent or translucent syringe body). Guide end 1835 may include opposed guide extensions 1837 which may deform outward resiliently to allow installation of the attachment 1800 on the syringe 1900. Guide extensions 1837 may include guide surfaces 1839 which may engage the curved underside syringe barrel 1910 and facilitate sliding movement of the attachment relative thereto. Guide extensions 1837 include a lateral position indicator 1838 (see FIG. 20 in addition) which coincide with lateral indicia 1913 on the sides of the syringe body to precisely indicate the position of the attachment, and thus the syringe plunger, when the system is viewed laterally from either side.

Figure 20:
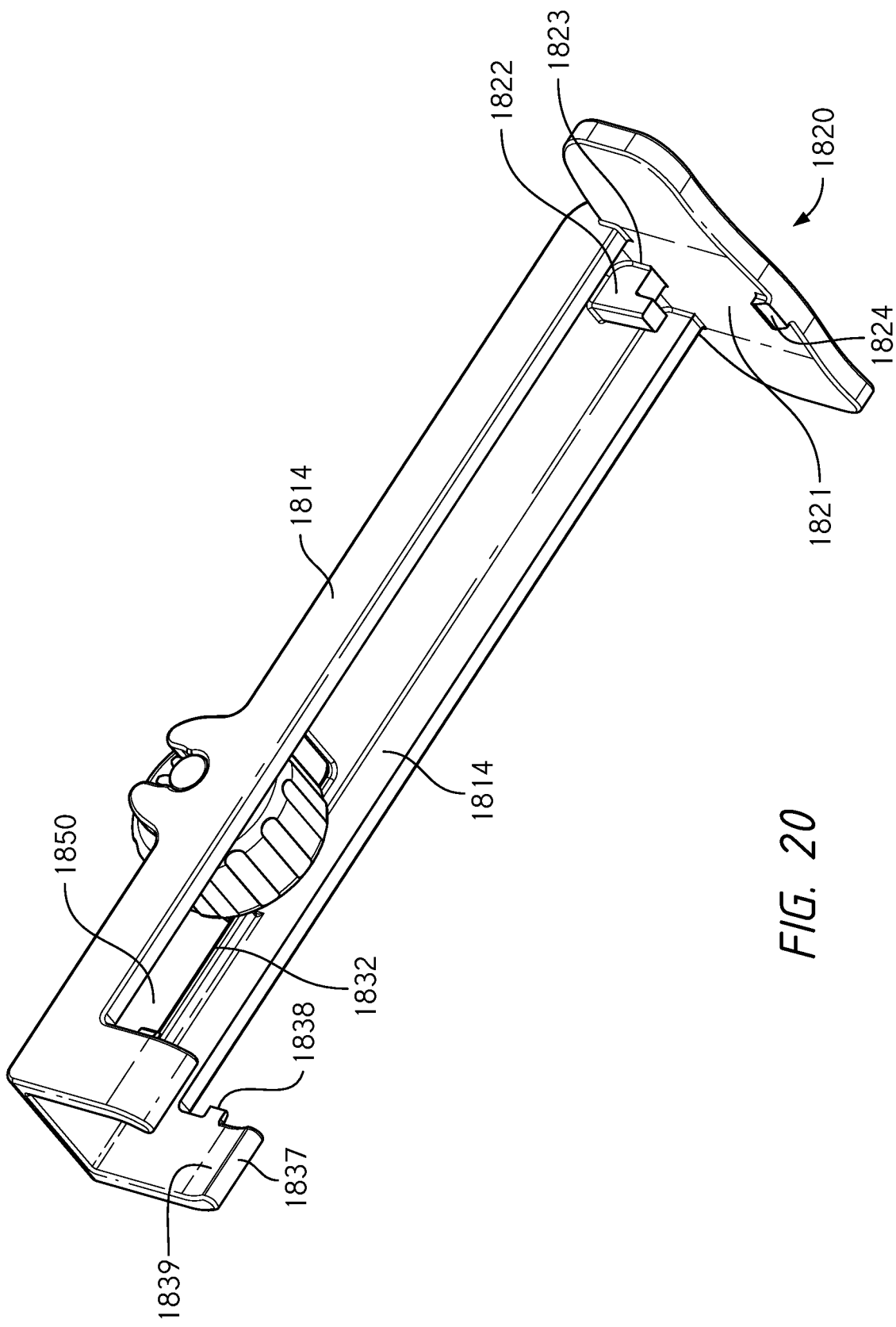
FIG. 20 is a perspective view of the attachment of FIG. 18 showing the underside thereof.
Figure 21:
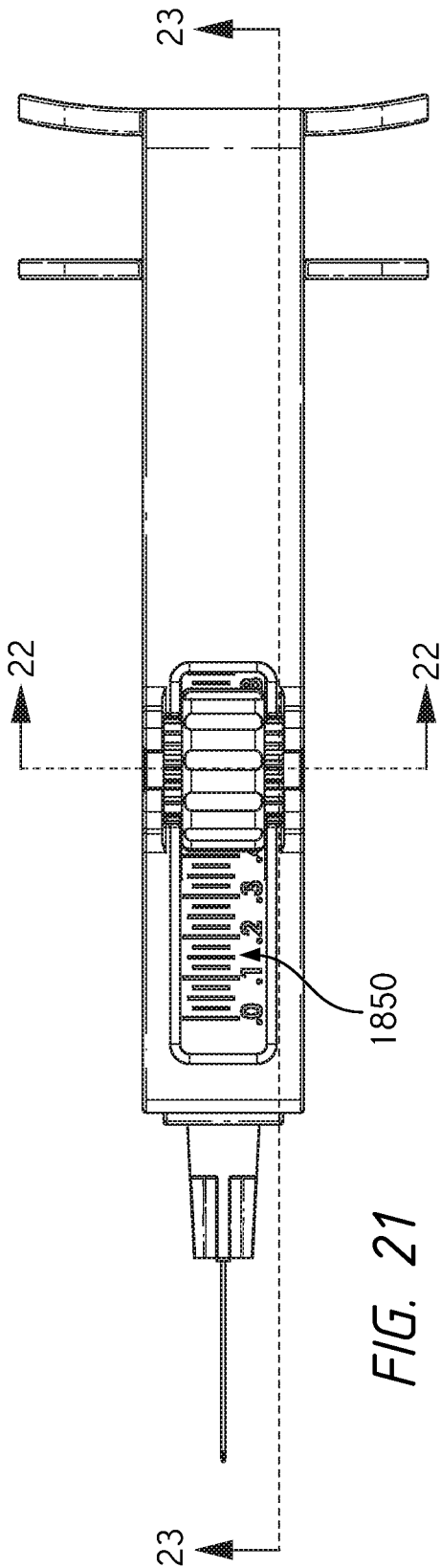
FIG. 21 is a top view of the attachment and syringe combination of FIG. 18.
Figure 22:
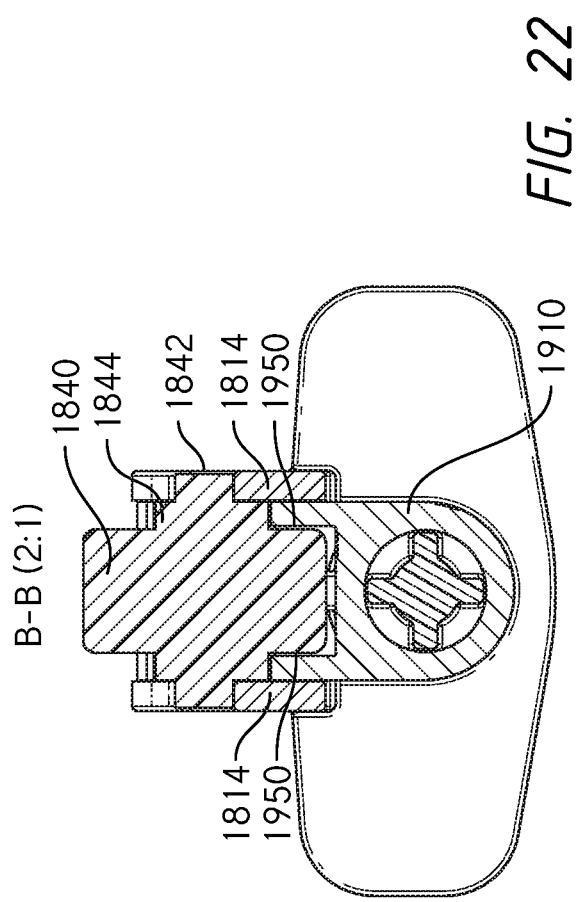
FIG. 22 is a cross-section at 22-22 in FIG. 21.
Figure 23:
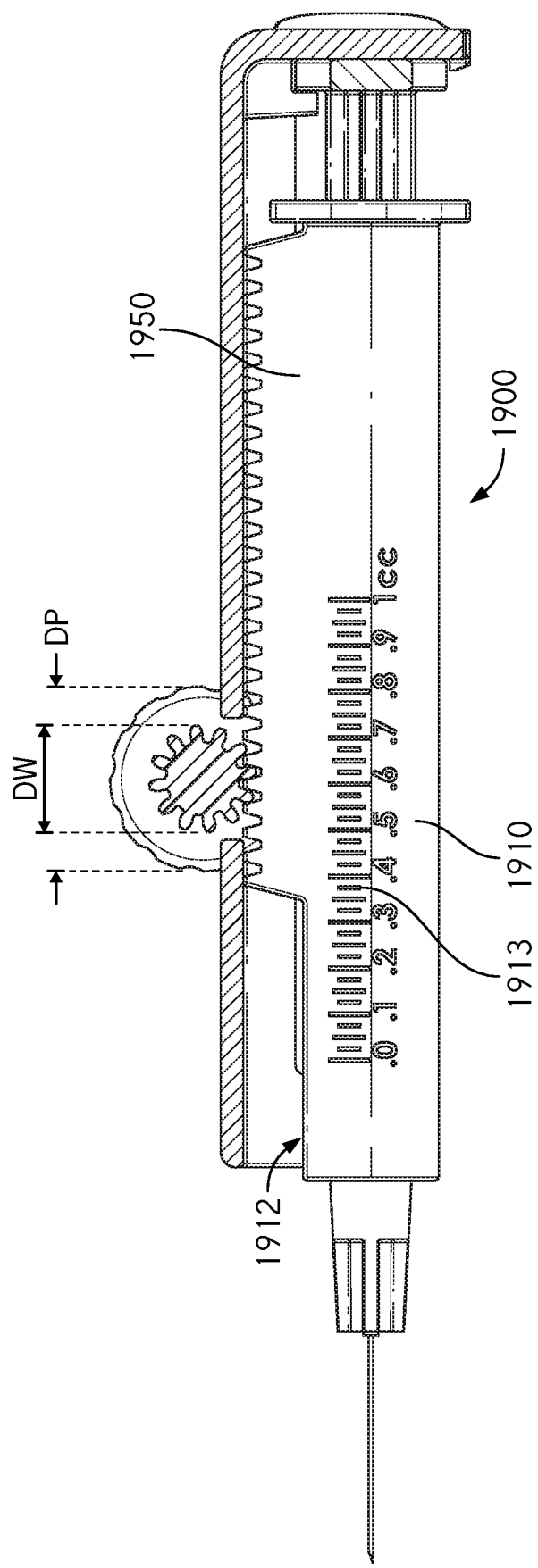
FIG. 23 is a cross-section at 23-23 in FIG. 21.
Figure 24:
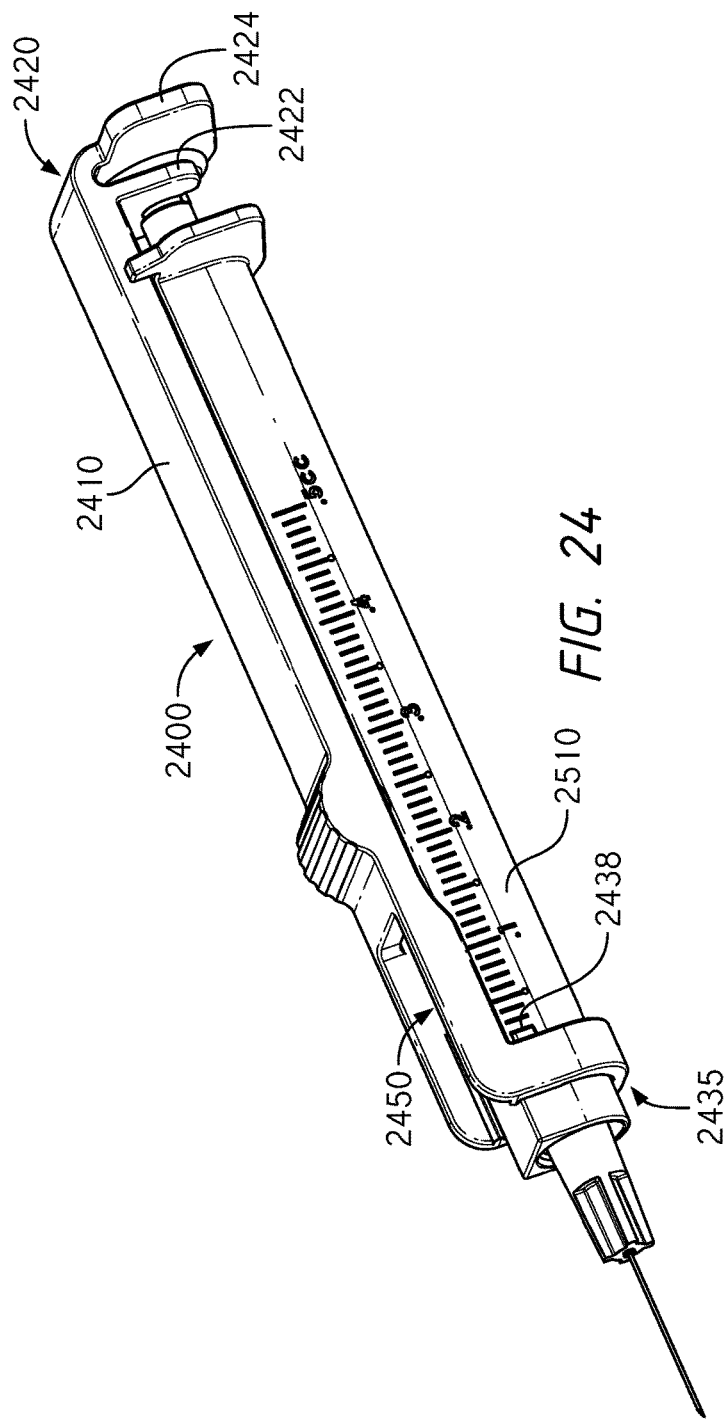
FIG. 24 is a perspective view of an attachment and syringe combination according to a fifth alternative.
Figure 25:
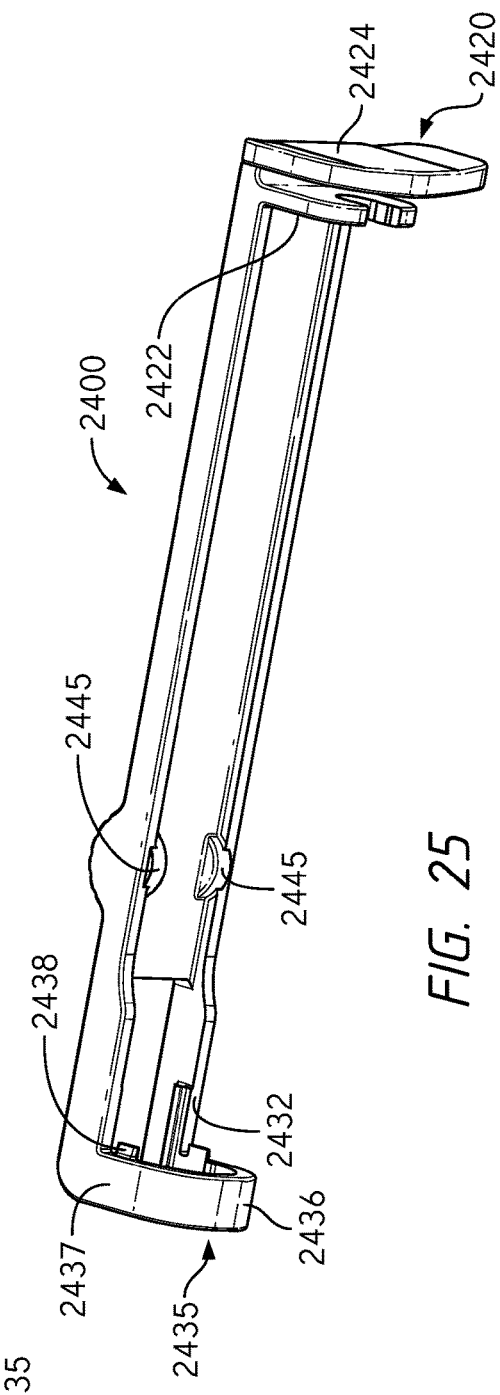
FIG. 25 is a perspective view of the attachment shown in FIG. 24.
Figure 28:
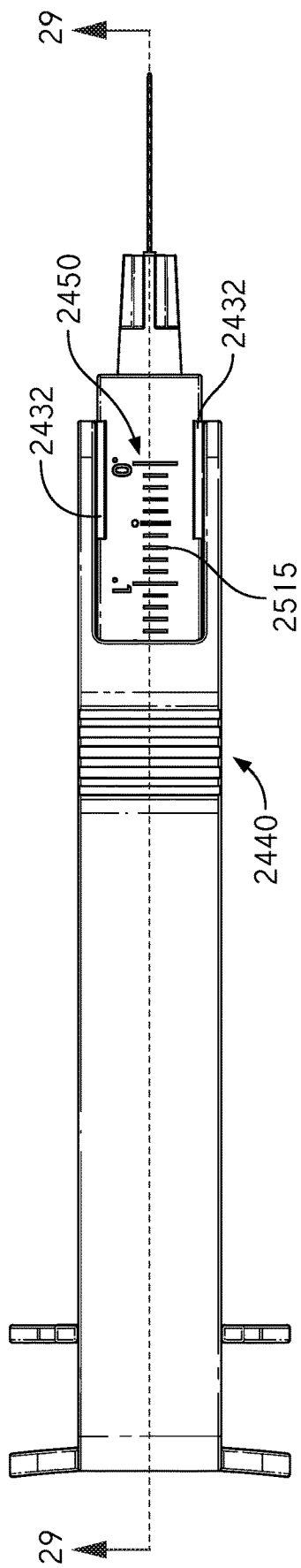
FIG. 28 is a top view of the syringe/attachment combination of FIG. 24.
Figure 29:
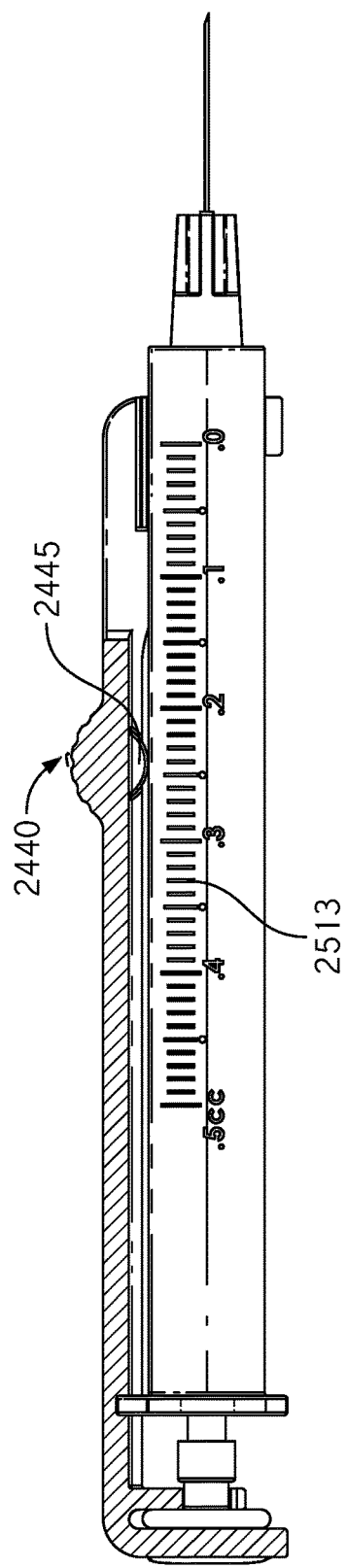
FIG. 29 is a cross-section at 29-29 in FIG. 28.

Referring particularly to FIGS. 20 and 23, a pair of guide rails 1832 may be formed on the interior of lateral walls 1814 for engaging and allowing sliding movement of the attachment relative to the upper surface 1912 (FIGS. 18 and 19) of syringe 1900. Guide rails 1832, in combination with the guide surfaces 1839 on the guide extensions 1837 provide for a snug fit of the attachment 1800 to the syringe 1900 while permitting sliding movement. To this end, guide rails and guide surfaces 1839 may be provided with friction reducing coatings, treatments or integrated materials to further enhance the operation and sliding movement and to prevent binding of the attachment relative to the syringe 1900.

Referring particularly to FIG. 20, the attachment plunger engaging end 1820 may include a plunger button retaining feature 1821 which may comprise a first projection 1822 forming a groove 1823 for receiving an upper edge of the plunger button 1942 (FIG. 20). A second projection 1824 may provide for a snap fit retention of the plunger button 1942 on the attachment plunger engaging end 1820.

Figure 18:
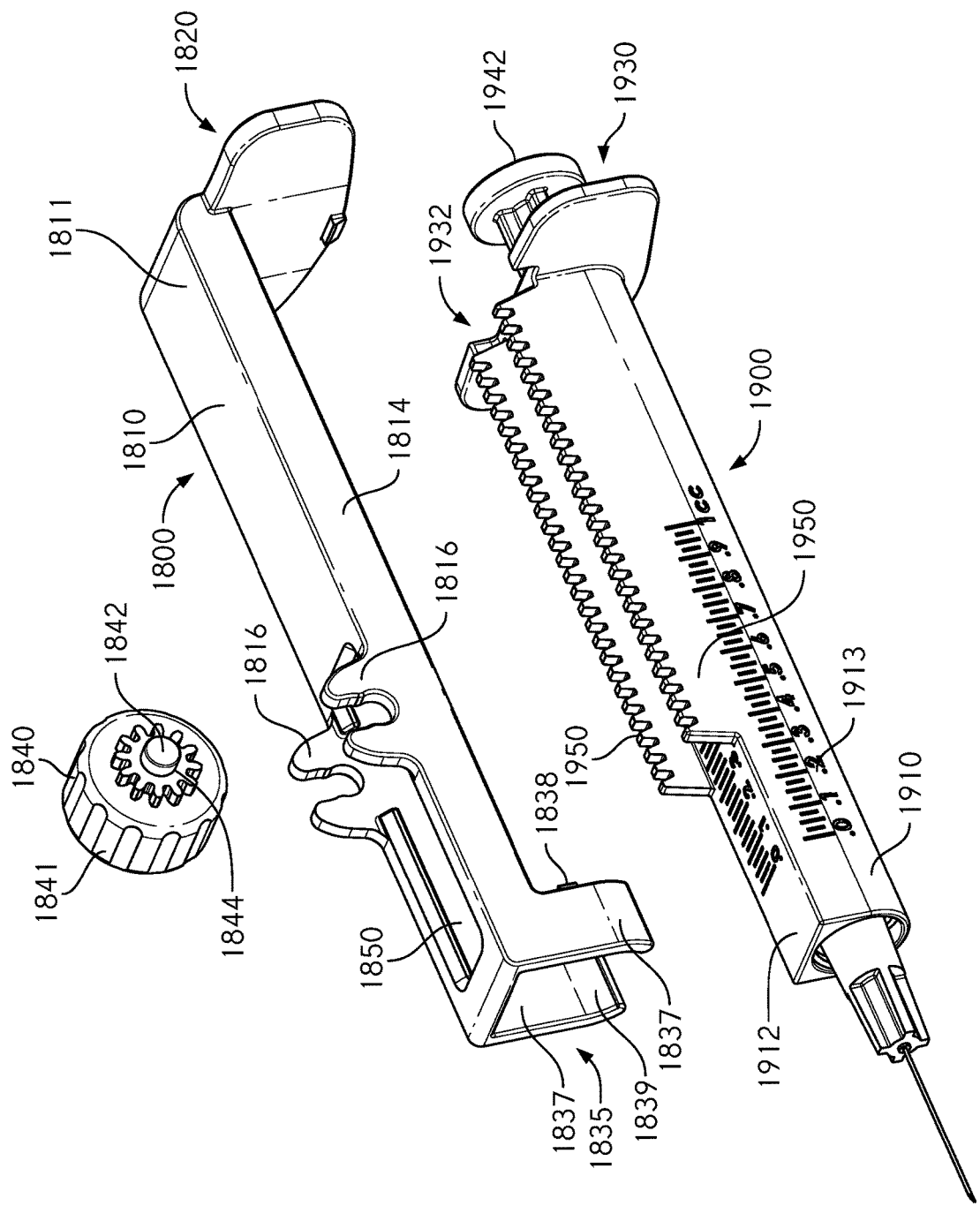
FIG. 18 is an exploded perspective view of a fourth alternative attachment and syringe combination.
Figure 19:
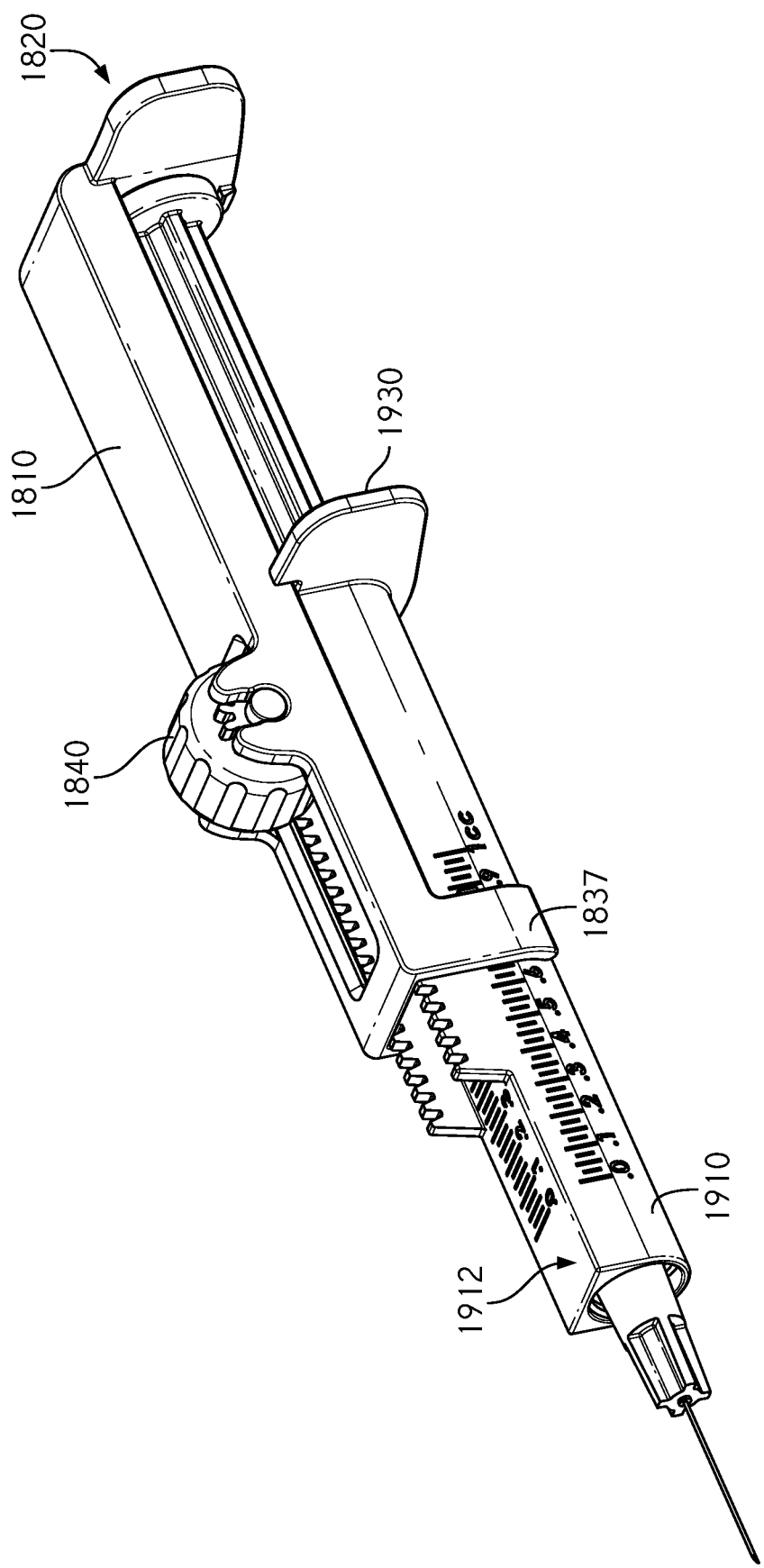
FIG. 19 is a perspective view of the attachment and syringe combination of FIG. 18, shown in an assembled and extended position.

According to aspects of the disclosure, the attachment 1800 may include an assist feature which may comprise a rolling element or wheel 1840 which may include an outer traction or gripping surface 1841, a central axle 1842 and one or more pinion gears 1844 (one shown in FIG. 18 with the understanding that another is hidden from view on an opposite side of wheel 1840). Wheel 1840 may be mounted for rotation within a pair of opposed journals 1816 extending upward from the attachment main body 1810. Journals 1816 may include a tapered receiving slot extending into circular recesses which may constitute snap fittings for respective sides of the axle 1842 for ease of assembly and dependable operation. As will be recognized, pinion gears 1844 engage respective toothed racks 1950 which extend upward from the syringe body 1900 and may be integrally formed therewith.

As will be recognized, the relationship of the wheel diameter DW (FIG. 23) to the pinion gear pitch diameter PW will provide a mechanical advantage to the user such that a force applied to the outer traction surface of the wheel (i.e., by the user's thumb during operation) will result in a multiplied force applied by the pinion gears to the racks, and thus a multiplied force applied to the syringe plunger to facilitate the dispensing of higher viscosity materials with reduced effort on the part of the user. Moreover, the wheel and pinion configuration provides a reduction in travel of the attachment relative to the syringe for a given degree of rotation of the wheel, thereby providing the user with more precise control of the plunger movement and dispensing of syringe contents.

According to aspects of the disclosure, attachment kits may be provided with wheels of different sizes and different pinion pitch diameters to permit customization by users on-site and for given syringe contents. Moreover, the disclosure contemplates different cooperating modes of the pinion gears and racks, including the use of intermediate gear elements (i.e., one or more intermediate gears between the pinion and the rack) to achieve desired operational characteristics, mechanical advantages and attachment movement characteristics.

As in the examples described above, tactile event features may be incorporated into the assist feature in order to provide a tactile sensation to the user for each incremental movement of the attachment relative to the syringe body. This may be achieved, for example, by providing a projection on the wheel journals that partially engages one or more teeth on the pinions and produces a clicking sound and tactile sensation each time a pinion tooth passes it, thus allowing the user to know precisely when an incremental rotation of the wheel occurs.

The features described in the above examples for enhancing visibility of the syringe plunger may also be applied to the example of FIGS. 18-23, such as providing highly visible coloring on the plunger end seal and providing an opaque bottom surface on the syringe against which the plunger may be viewed.

FIGS. 24-29 illustrate an attachment and attachment/syringe combination in accordance with another aspect of the disclosure. This configuration provides an attachment that may be slidably secured to a syringe to permit a user to operation the syringe from a lateral position using sliding movement of the thumb and fingers of one hand, for example. This configuration may be particularly suitable for self-administered insulin injections in extremities (i.e., arms or legs) of the human body where single hand operation of a traditional syringe (thumb on the plunger button) does not facilitate precise dispensing of syringe contents.

An example attachment 2400 may comprise an elongate main body 2410 having a syringe plunger engaging end 2410 and a guide end 2435. Syringe plunger engaging end 2420 may include a first fastening wall 2422 extending generally orthogonally from the main body 2410 and including a recess formed therein for receiving and retaining in a snap fit fashion the shaft of the syringe plunger 2542 (FIG. 26). A second wall 2424 may extend from the main body 2410 for abutting the plunger button 2541 and may form a plunger button receiving recess or groove 2425 for receiving and retaining the plunge button therein. A viewing window 2450 (FIGS. 24, 26 and 28) may be formed in the attachment main body and provides for viewing of the upper flat surface of the syringe, the indicia thereon, and where the syringe is made of a transparent or translucent material, the syringe plunger traveling in the syringe lumen. In addition, lateral position indicators 2438 (FIGS. 24-26) may coincide with the lateral indicia on the sides of the syringe body and provide for precise indication of attachment position, plunger position and thus dosage during use.

Guide end 2435 may include a continuous guide ring 2436 extending across two lateral guide extensions 2437 extending from the attachment main body 2410. Lateral guide extensions 2437 and guide ring 2436 may include guide surfaces on their interior walls for engaging the syringe body and facilitating sliding movement of the attachment relative thereto. Attachment 2400 may include a thumb-engaging projection 2440, having a semi-circular shape generally and including a gripping or non-slip surface 2441. Disposed on the underside of the attachment main body 2410 and in the vicinity of or coinciding with the thumb-engaging projection, may be a pair of guiding projections 2445 (FIGS. 25 and 29) which may have a circular surface for engaging the flat surface 2512 of the syringe 2500. Attachment 2500 may also include a pair of guide rails 2432 for engaging the syringe upper flat surface 2512. The guiding projections 2445, guide rails 2432 and guiding surfaces of the guide extensions 2437 and guiding ring 2435, provide for stable and smooth movement of the attachment relative to the syringe.

FIG. 26 illustrates an installation step for installing the attachment 2400 on the syringe 2500 whereby the needle end of the syringe is first inserted through the attachment guide end 2435. Next, the attachment plunger engaging end is rotated downward (clockwise in FIG. 26) until the plunger shaft is snap fit into the first wall, thus retaining the syringe plunger therein.

FIG. 27 illustrates further details of an example syringe suitable for use with the attachment described herein. The rear flange 2531 on the syringe may include a recess 2532 for accommodating the attachment main body 2410 and permit sliding movement of the attachment 2400 relative to the syringe 2500. The upper flat surface 2512 provides for ease of reading the indicia thereon as well as a stable guiding surface for the guiding projections 2445 (FIG. 25) and guiding rails 2432 (FIG. 25) of the attachment to engage. Moreover, it will be recognized that the physical dimensions of the syringe 2500 are advantageous particularly for self-administering of insulin and other materials in low dosage applications. More particularly, the syringe is provided with a relatively small lumen and a relatively large outer syringe body dimension (width and diameter of rounded portion), such that the syringe width and length reduce the potential for mishandling and injury. Moreover, the small lumen diameter results in a longer plunger travel for the small volume, thus providing more visibility for smaller gradations and more precise control by the user of dosage based on the sliding movement of the attachment.

According to an aspect of the disclosure, the attachment described above with regard to FIGS. 24-29 may be provided with a tactile event feature to indicate incremental movement to the user in a tactile and/or audible manner. For example, the indicia 2515 on the flat surface 2512 may include major gradations (i.e., every 0.1 cc) which extend laterally across the flat surface and are raised or recessed relative to the flat surface. The guide projections 2445 (FIG. 25) may be positioned such that they encounter the raised or recessed gradations as the attachment slides relative to the syringe body and generate a tactile sensation and/or clicking noise that is sensed by the user. This enhances the precise control available to the user. As a further alternative a rolling ball or element may be provided on the underside of the attachment to roll over the raised or recessed gradations as the attachment moves relative to the syringe body.

Although the present implementations have been described with reference to specific example embodiments, it will be evident that various modifications and changes may be made to these embodiments without departing from the broader spirit and scope of the invention as set forth in the claims. Accordingly, the specification and drawings are to be regarded put forth in an illustrative sense rather than a restrictive sense.

What is claimed is:

1. A system comprising:
    a syringe comprising a syringe body and a plunger, the syringe body having an axially extending flat surface and defining a syringe lumen;
    an attachment comprising:
        a main body having a plunger engaging end adapted to engage the plunger and a guide end adapted to receive the syringe body and support the attachment for sliding movement on the syringe body;
        a thumb-engaging projection for permitting a user to apply force to the attachment to cause axial movement relative to the syringe body;
        a viewing window formed in the main body for allowing the user to view the syringe flat surface;
        a pair of guide rails on the main body for supporting the attachment for sliding movement on the syringe flat surface;
        a first fastening wall extending generally orthogonally from the main body and including a recess formed therein for receiving and retaining a shaft of the syringe plunger; and
        a second wall extending from the main body and arranged to abut a plunger button on the syringe plunger.

2. The system of claim 1, wherein the attachment further comprises at least one guiding projection disposed near the thumb-engaging projection for supporting the attachment for sliding movement on the syringe body flat surface.

3. The system of claim 1, further comprising a tactile indicator for generating a tactile event to the user as the main body moves relative to the syringe body.

4. The system of claim 1, wherein the attachment main body guide end includes a U-shaped extension for receiving the syringe body.

5. The system of claim 1, wherein the viewing window is arranged to display the flat surface and an end of the plunger disposed in the syringe lumen.

6. The system of claim 1, wherein the syringe includes a flange and a recess in the flange for accommodating the attachment main body when the attachment is in an installed position.

7. The system of claim 1, further comprising a pair of guiding projections disposed on a side of the attachment that is opposite the thumb-engaging projection and arranged to engage the syringe flat surface.

8. The system of claim 7, wherein the guiding projections each have a circular surface for engaging the syringe body flat surface.

9. The system of claim 1, wherein the syringe body is provided with lateral indicia on a side thereof and wherein the attachment is provided with at least one lateral position indicator that coincides with the lateral indicia on the side of the syringe body.

10. The system of claim 1, wherein the guide end includes a continuous guide ring joining two lateral guide extensions extending from the attachment main body, the guide ring and lateral guide extensions providing a continuous guide surface adapted to guide the attachment on the syringe body.

11. The system of claim 1, wherein the syringe body flat surface is provided with indicia thereon, and where the viewing window is arranged to permit viewing of the syringe body flat surface as the attachment moves relative to the syringe body.

12. The system of claim 1, wherein the viewing window is arranged to permit viewing of an end of the syringe plunger within the syringe lumen as the syringe plunger travels within the syringe lumen.

13. The system of claim 1, further comprising lateral position indicators that coincide with lateral indicia on at least one side of the syringe body.

14. The system of claim 1, wherein the thumb-engaging projection has a semi-circular shape.

15. The system of claim 14, wherein the thumb-engaging portion includes a gripping surface.

16. The system of claim 1, wherein the syringe includes a lumen having a diameter and wherein the plunger is adapted to travel a plunger travel length within the lumen, and wherein the lumen diameter and plunger travel length are selected to facilitate dispensing a volume, as indicated by indicia on the syringe, of no more than 0.5 ml.

17. The system of claim 16, wherein the indicia include marks on the syringe body corresponding to 0.01 ml increments of displacement.

18. The system of claim 1, further comprising a tactile event feature to indicate incremental movement to the user in a tactile and/or audible manner.

19. The system of claim 18, wherein the tactile event feature comprises at least one guide projection positioned to encounter raised or recessed gradations on the syringe body as the attachment slides relative to the syringe body.

* * * * *